United States Patent
Frey et al.

(10) Patent No.: US 9,615,938 B2
(45) Date of Patent: Apr. 11, 2017

(54) METHODS AND APPARATUS FOR INSERTION OF IMPLANT MATERIAL

(71) Applicants: George Frey, Englewood, CO (US); Benjamin Majors, Denver, CO (US); Charles O'Neil, Littleton, CO (US); Geoff Lai, Lakewood, CO (US); Russ Rydin, Highlands Ranch, CO (US)

(72) Inventors: George Frey, Englewood, CO (US); Benjamin Majors, Denver, CO (US); Charles O'Neil, Littleton, CO (US); Geoff Lai, Lakewood, CO (US); Russ Rydin, Highlands Ranch, CO (US)

(73) Assignee: MIGHTY OAK MEDICAL, INC., Englewood, CO (US)

( * ) Notice: Subject to any disclaimer, the term of this patent is extended or adjusted under 35 U.S.C. 154(b) by 200 days.

(21) Appl. No.: 14/286,639

(22) Filed: May 23, 2014

(65) Prior Publication Data
US 2014/0257313 A1    Sep. 11, 2014

Related U.S. Application Data

(63) Continuation-in-part of application No. 12/434,328, filed on May 1, 2009, now Pat. No. 8,734,515.
(Continued)

(51) Int. Cl.
*A61F 2/46* (2006.01)
*A61F 2/44* (2006.01)
(Continued)

(52) U.S. Cl.
CPC .......... *A61F 2/4611* (2013.01); *A61B 17/025* (2013.01); *A61B 17/7077* (2013.01);
(Continued)

(58) Field of Classification Search
CPC ... A61F 2/4611; A61F 2002/4627–2002/4628; A61B 2017/0256; A61B 17/025
See application file for complete search history.

(56) References Cited

U.S. PATENT DOCUMENTS

| 3,486,505 A | 12/1969 | Morrison |
| 5,345,927 A * | 9/1994 | Bonutti ............... A61B 17/0218 600/204 |

(Continued)

OTHER PUBLICATIONS

International Search Report and Written Opinion for International (PCT) Application No. PCT/US2009/042570 mailed Jun. 25, 2009, 10 pages.
(Continued)

*Primary Examiner* — Christopher D Prone
(74) *Attorney, Agent, or Firm* — Sheridan Ross P.C.

(57) ABSTRACT

Various surgical devices and methods for facilitating distraction of adjacent vertebrae and/or insertion of an intervertebral implant material therebetween are disclosed. The devices include an elongated barrel having a cannula. A distal end of the barrel is configured to engage the adjacent vertebrae. Slots may be formed on at least a portion of the barrel such that at least the distal end of the barrel may be expanded to distract vertebrae. In one embodiment, an inner member is reciprocally positioned within the barrel. The inner member includes features that engage one or more surfaces of the barrel to expand the distal end of the barrel as the inner member moves with respect to the barrel. In some embodiments, cams are used to expand the distal end of the barrel.

12 Claims, 36 Drawing Sheets

Related U.S. Application Data

(60) Provisional application No. 61/051,036, filed on May 7, 2008.

(51) Int. Cl.
    *A61B 17/02*     (2006.01)
    *A61B 17/70*     (2006.01)
    *A61B 17/34*     (2006.01)

(52) U.S. Cl.
    CPC .......... *A61F 2/4455* (2013.01); *A61F 2/4601* (2013.01); *A61B 17/3468* (2013.01); *A61B 2017/0256* (2013.01); *A61F 2002/448* (2013.01); *A61F 2002/4627* (2013.01)

(56) References Cited

U.S. PATENT DOCUMENTS

| | | |
|---|---|---|
| 5,549,679 A | 8/1996 | Kuslich |
| 5,653,762 A | 8/1997 | Pisharodi |
| 5,658,336 A | 8/1997 | Pisharodi |
| 5,876,440 A | 3/1999 | Feingold |
| 6,309,421 B1 | 10/2001 | Pisharodi |
| 6,368,325 B1 | 4/2002 | McKinley et al. |
| 6,436,119 B1 * | 8/2002 | Erb .................... A61B 17/3417 606/185 |
| 6,595,998 B2 | 7/2003 | Johnson et al. |
| 6,887,248 B2 | 5/2005 | McKinley et al. |
| 6,997,929 B2 | 2/2006 | Manzi et al. |
| 7,153,305 B2 | 12/2006 | Johnson et al. |
| 7,311,713 B2 | 12/2007 | Johnson et al. |
| 8,734,515 B2 | 5/2014 | Frey |
| 2002/0151856 A1 | 10/2002 | Gollobin |
| 2002/0161375 A1 | 10/2002 | Ralph et al. |
| 2005/0187559 A1 | 8/2005 | Raymond et al. |
| 2005/0216088 A1 | 9/2005 | McKinley et al. |
| 2005/0283161 A1 | 12/2005 | McCombe et al. |
| 2006/0129238 A1 | 6/2006 | Paltzer |
| 2007/0142841 A1 | 6/2007 | Reitzig et al. |
| 2007/0213739 A1 | 9/2007 | Michelson |
| 2007/0270873 A1 | 11/2007 | Flickinger et al. |
| 2007/0270875 A1 | 11/2007 | Bacher et al. |
| 2007/0276406 A1 | 11/2007 | Mahoney et al. |
| 2008/0071279 A1 | 3/2008 | Bandeira et al. |
| 2008/0114371 A1 | 5/2008 | Kluger |
| 2008/0132902 A1 | 6/2008 | Bertagnoli et al. |
| 2008/0161817 A1 | 7/2008 | Parsons et al. |

OTHER PUBLICATIONS

International Preliminary Report on Patentability for International (PCT) Application No. PCT/US2009/042570 mailed Nov. 18, 2010, 10 pages.
Examination Report for Australia Patent Application No. 2009244557, dated Jul. 10, 2013 5 pages.
Notice of Acceptance for Australia Patent Application No. 2009244557, dated Jan. 14, 2014 2 pages.
Official Action for Canadian Patent Application No. 2,722,918 dated Dec. 7, 2012 2 pages.
Notice of Allowance for Canada Patent Application No. 2,722,918, dated Sep. 30, 2013 1 page.
Search Report for European Patent Application No. 09743348.6, dated May 24, 2013 5 pages.
Official Action for European Patent Application No. 09743348.6, dated Jun. 4, 2013 8 pages.
Intention to Grant for European Patent Application No. 09743348.6, dated Mar. 25, 2014 6 pages.
Official Action with English Translation for Japan Patent Application No. 2011-508565, mailed Jun. 28, 2013 6 pages.
Official Action with English Translation for Japan Patent Application No. 2011-508565, mailed Mar. 4, 2014 4 pages.
Official Action for U.S. Appl. No. 12/434,328 mailed Oct. 3, 2011, 8 pages. Restriction Requirement.
Official Action for U.S. Appl. No. 12/434,328 mailed Jan. 3, 2012, 11 pages.
Official Action for U.S. Appl. No. 12/434,328 mailed Aug. 24, 2012, 10 pages.
Notice of Allowance for U.S. Appl. No. 12/434,328, mailed Jan. 17, 2014 10 pages.
Official Action for Australia Patent Application No. 2014202207, dated Feb. 26, 2015 3 pages.
Official Action for Canada Patent Application No. 2,846,942, dated Nov. 16, 2015 4 pages.
International Search Report and Written Opinion for International (PCT) Patent Application No. PCT/US15/31462, mailed Aug. 12, 2015 8 pages.

\* cited by examiner

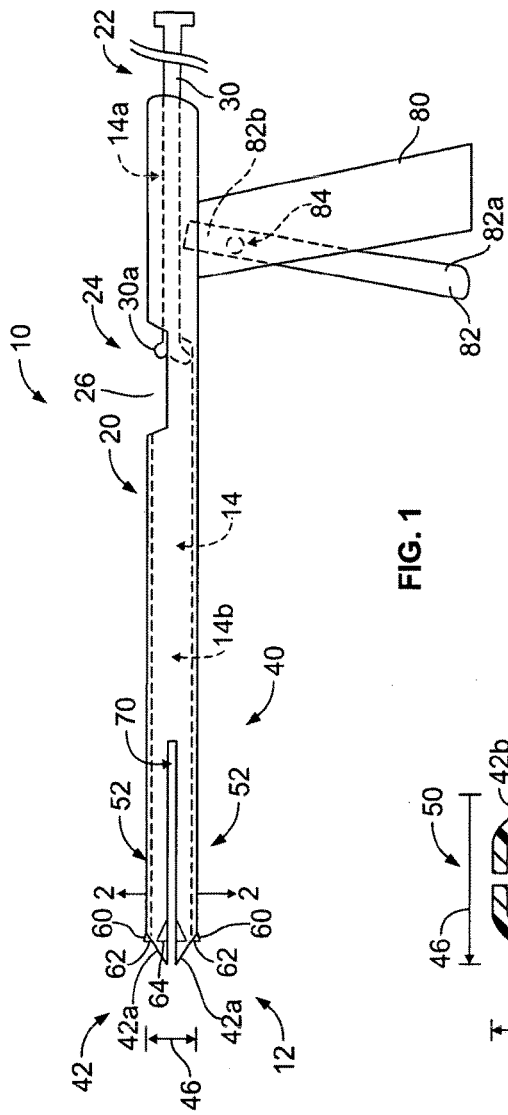
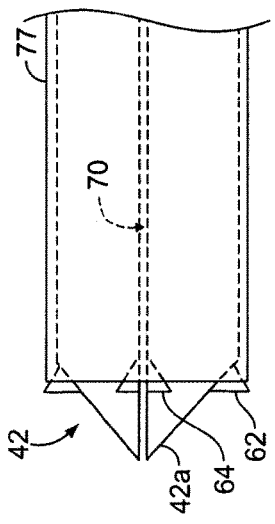
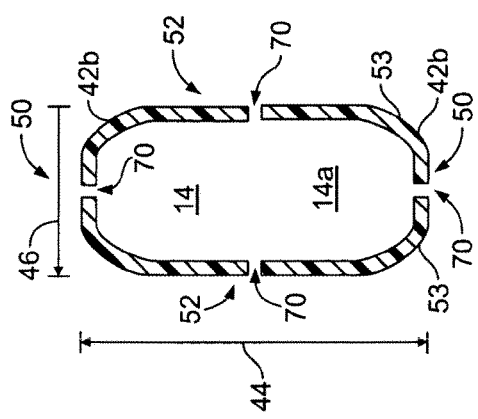

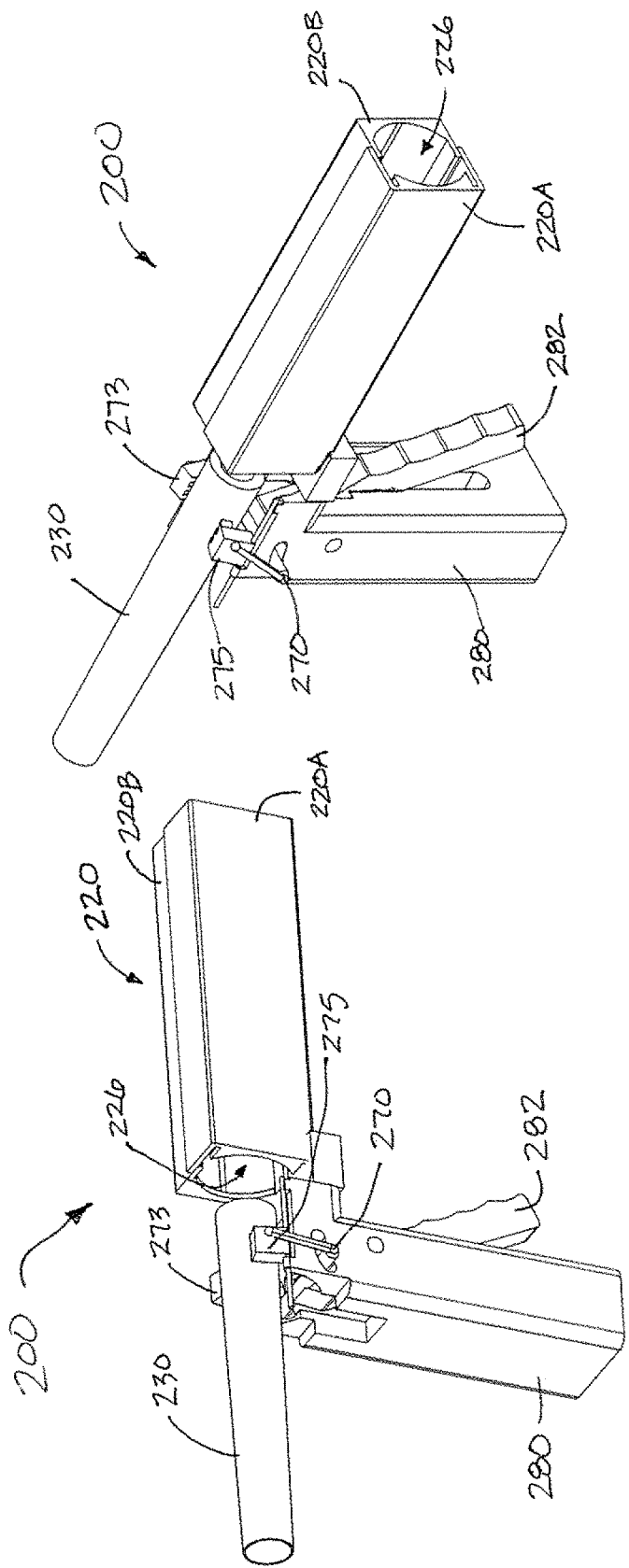

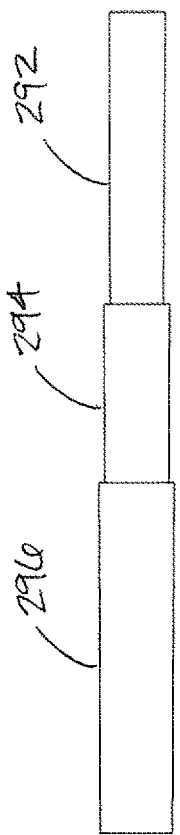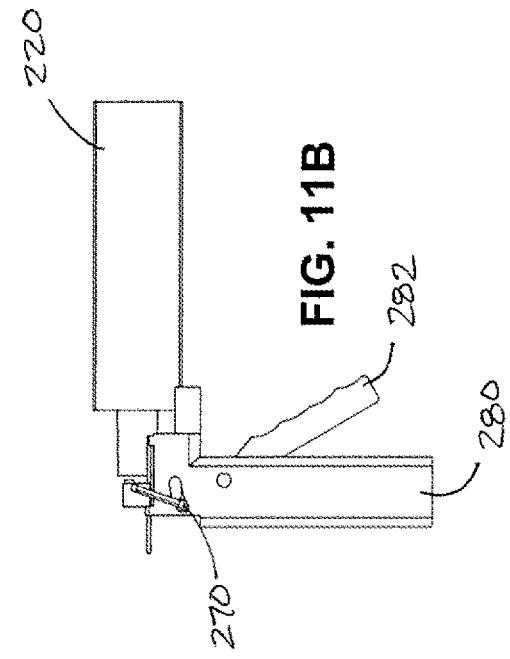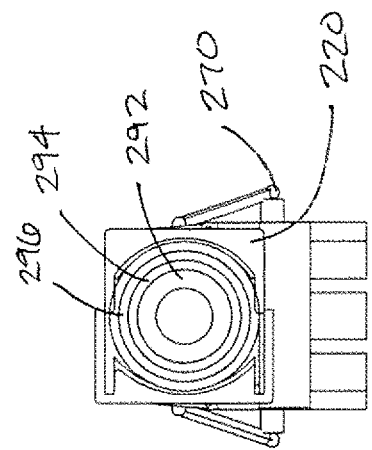

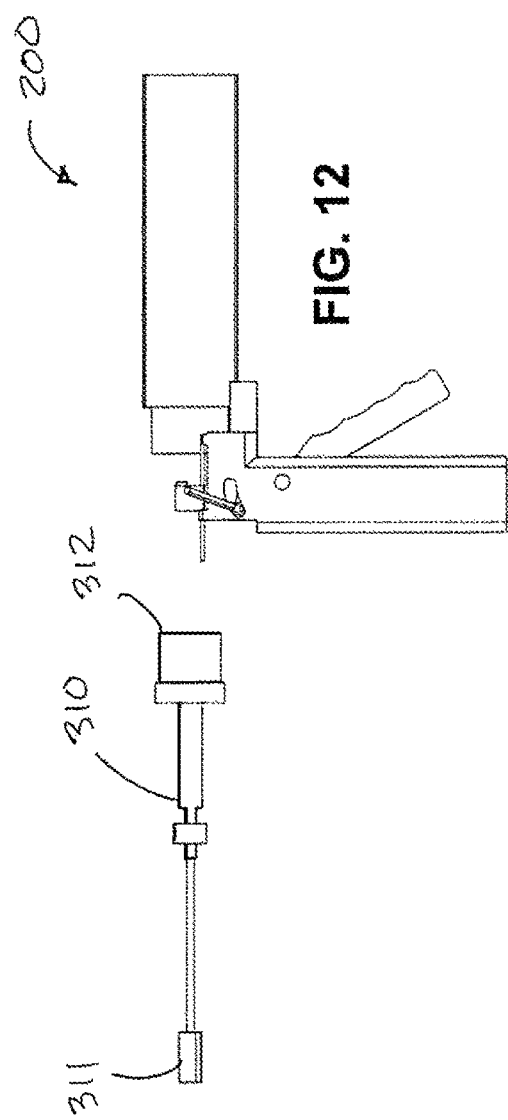

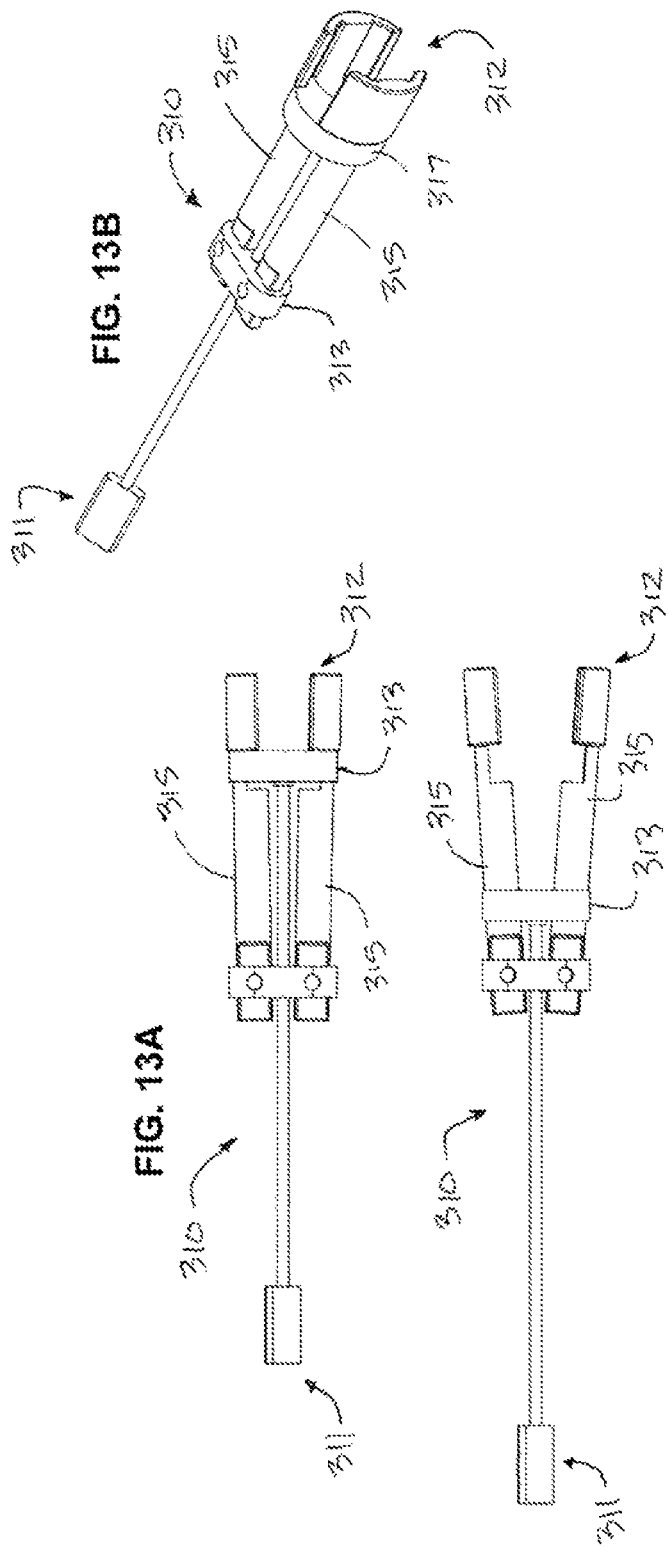

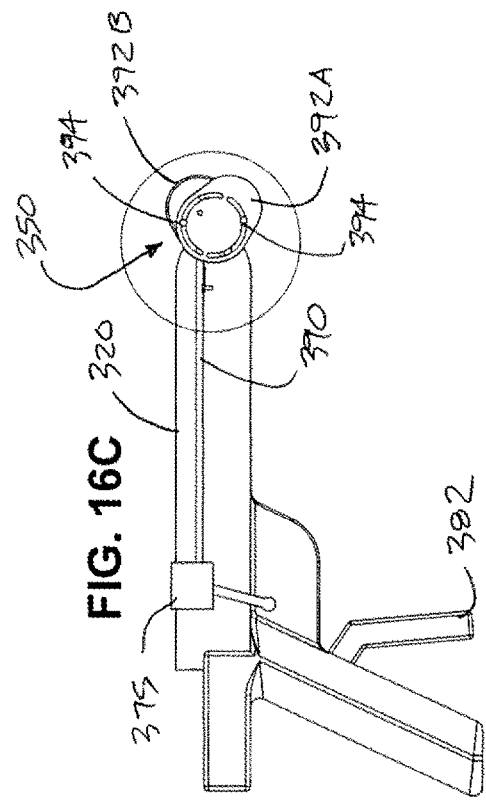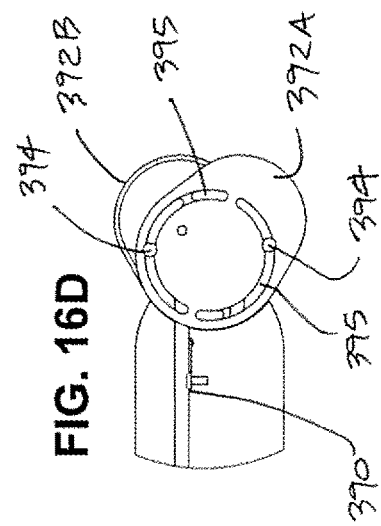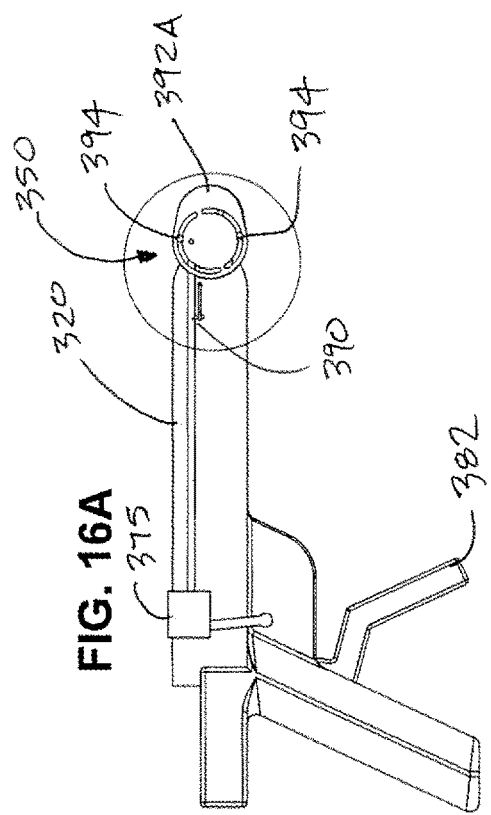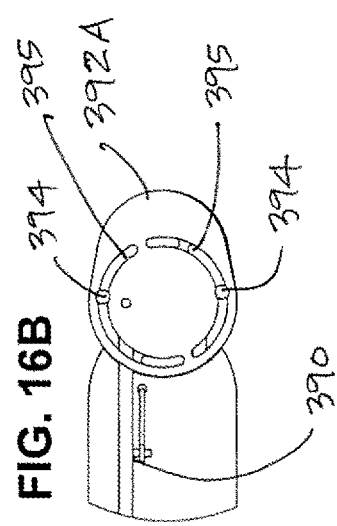
FIG. 16C
FIG. 16D
FIG. 16A
FIG. 16B

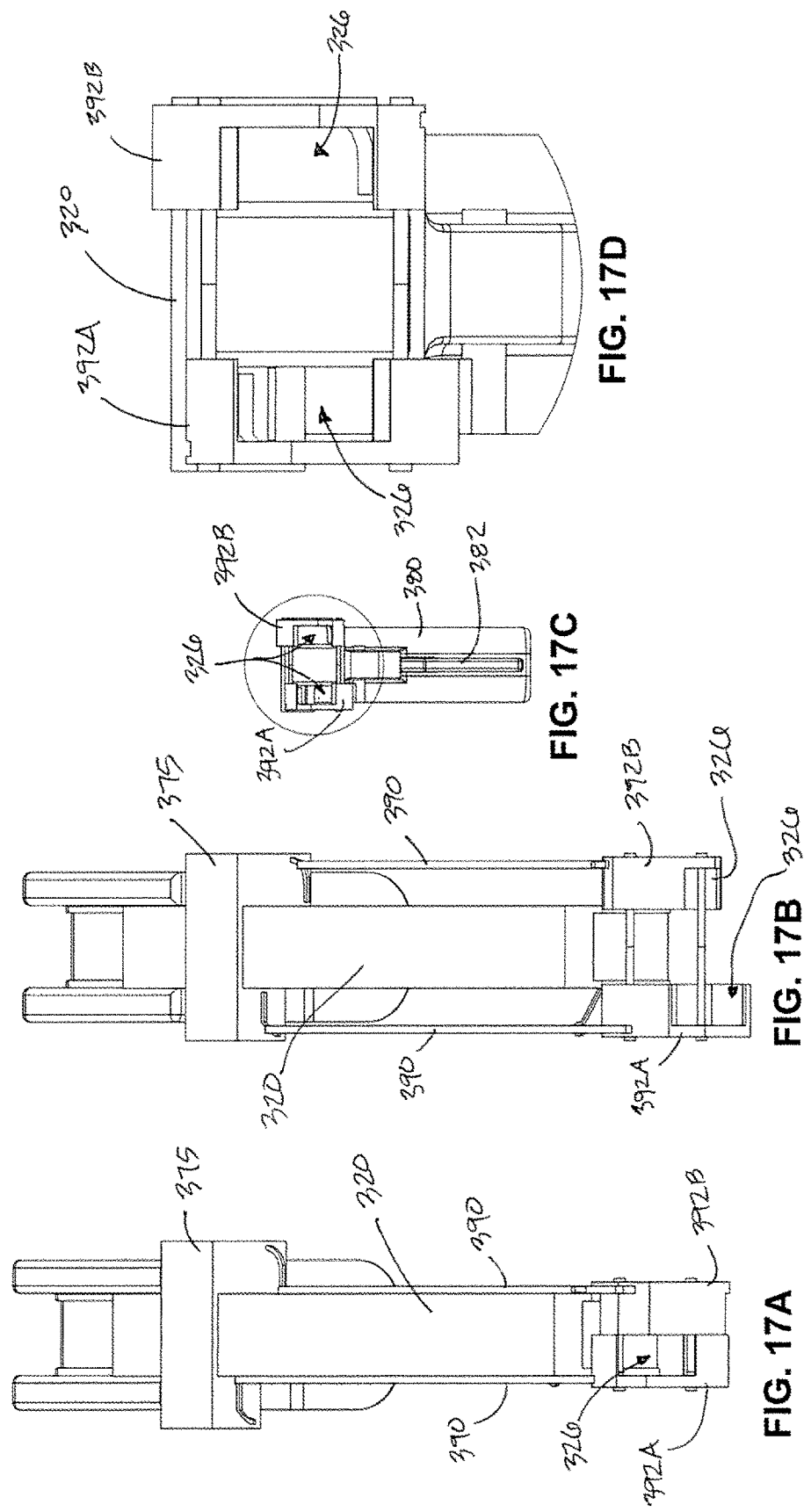

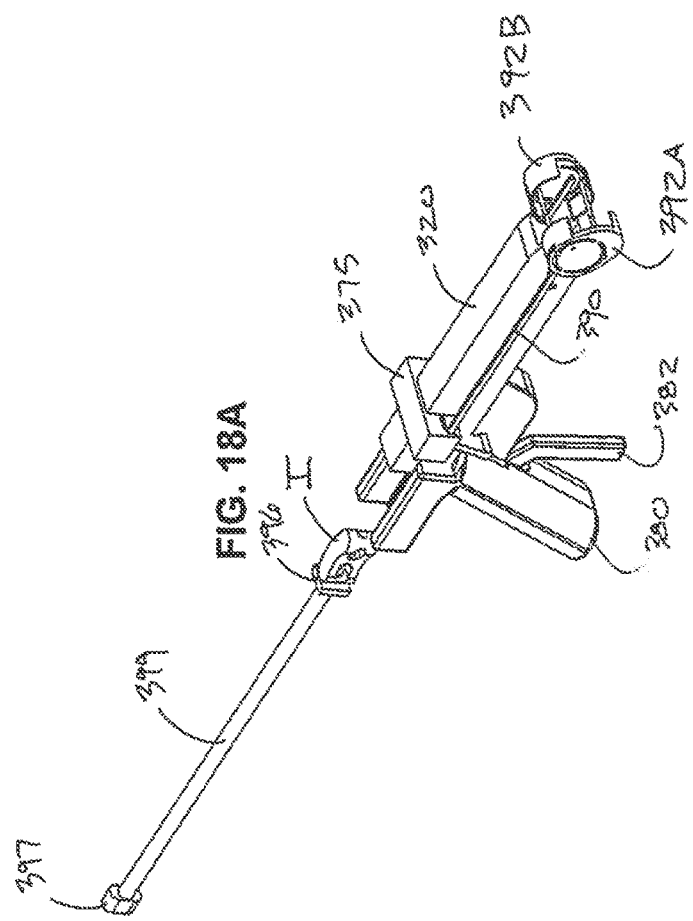
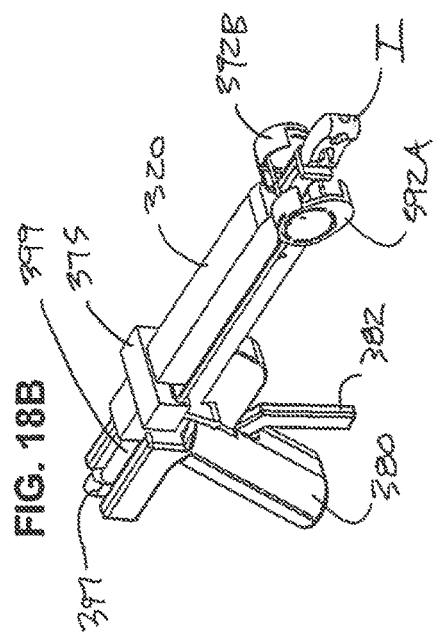

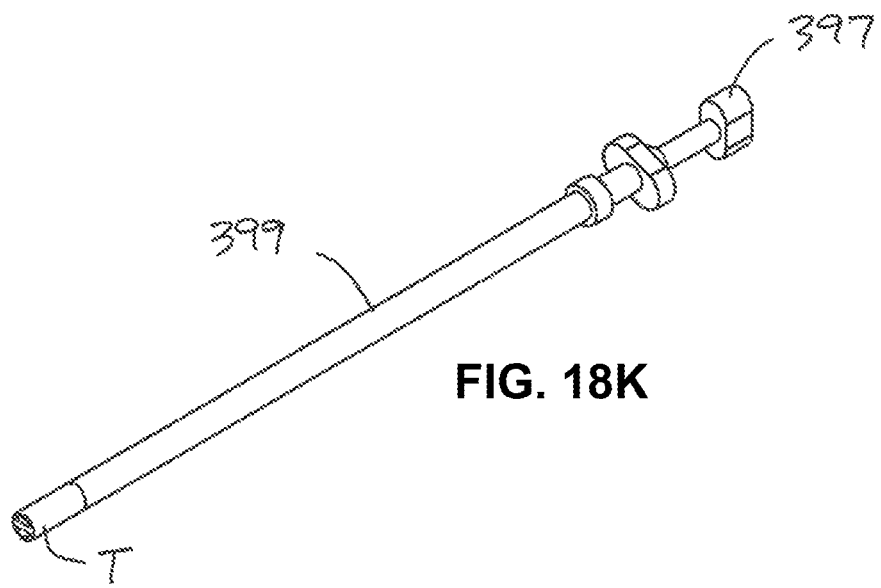
FIG. 18K
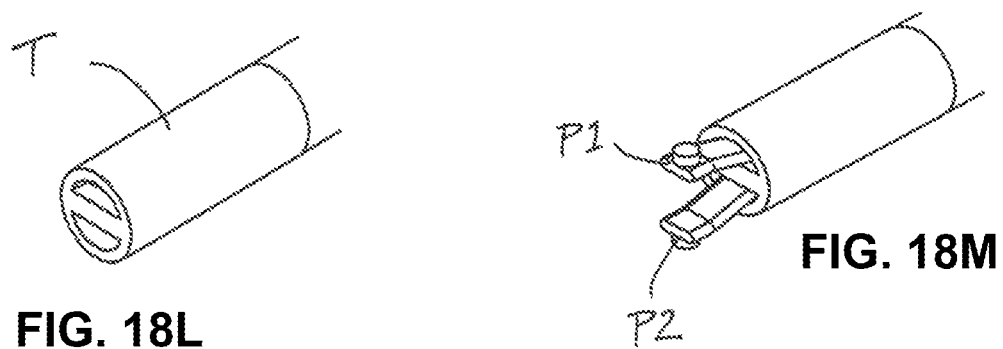
FIG. 18L
FIG. 18M
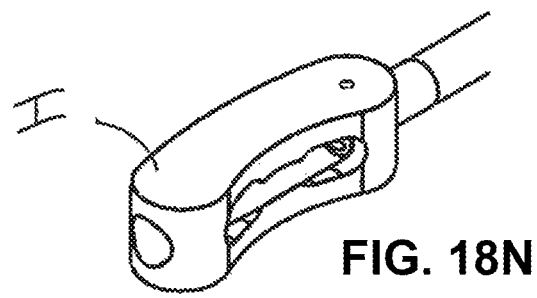
FIG. 18N

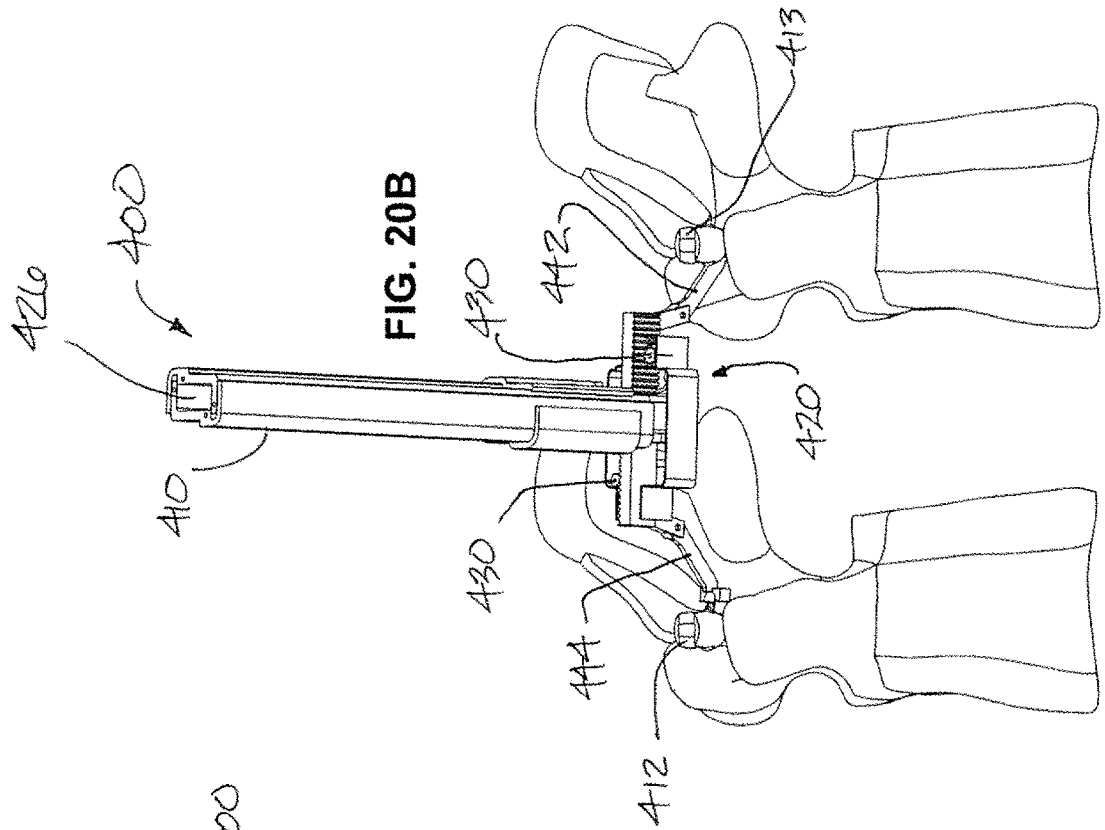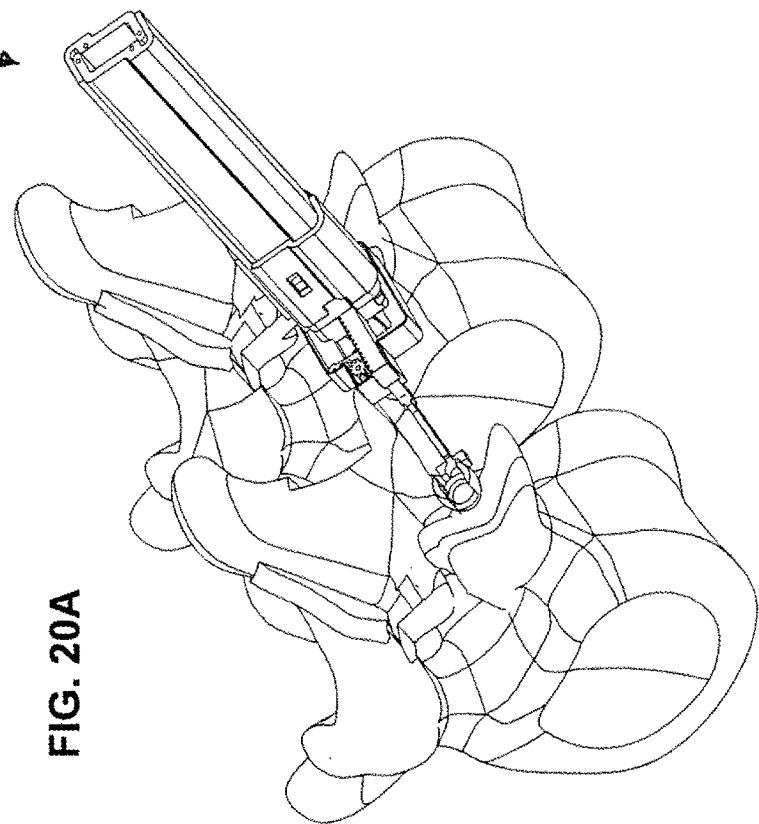

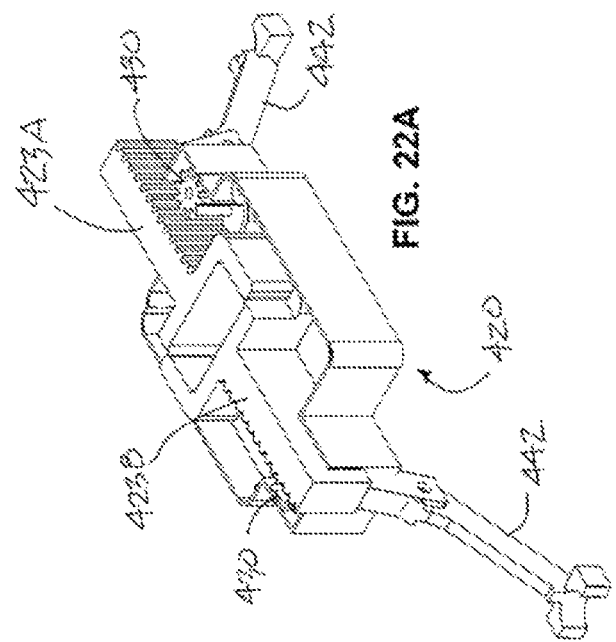
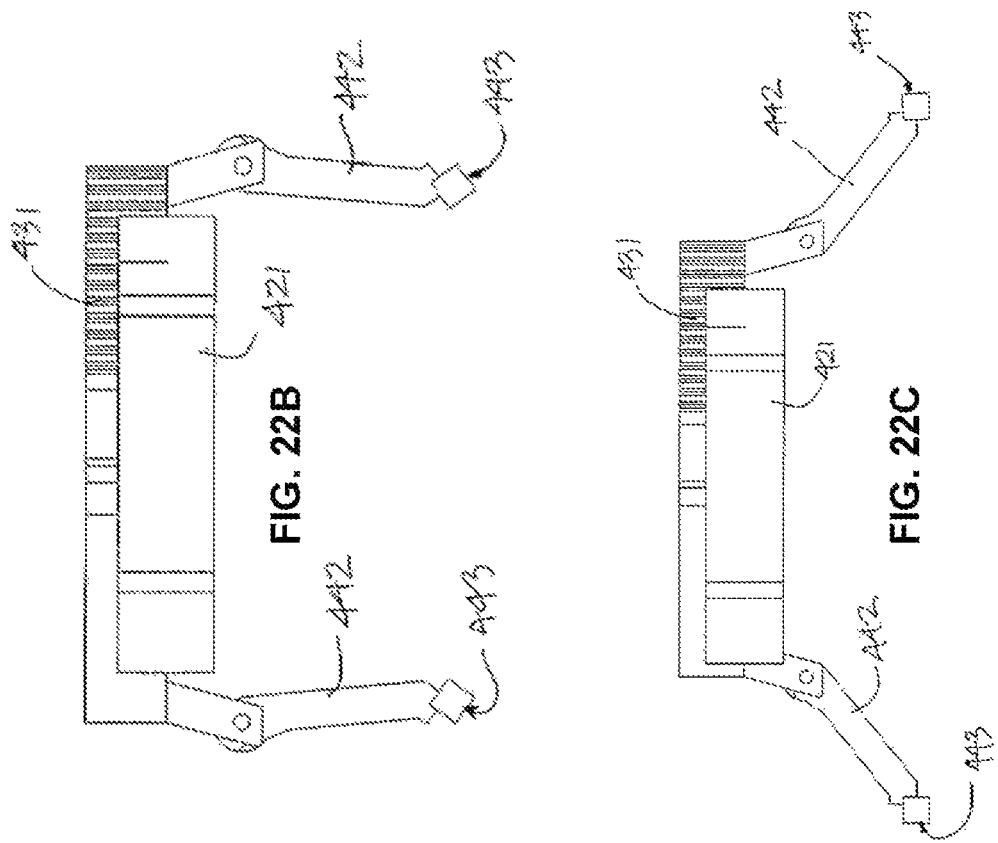
FIG. 22A
FIG. 22B
FIG. 22C

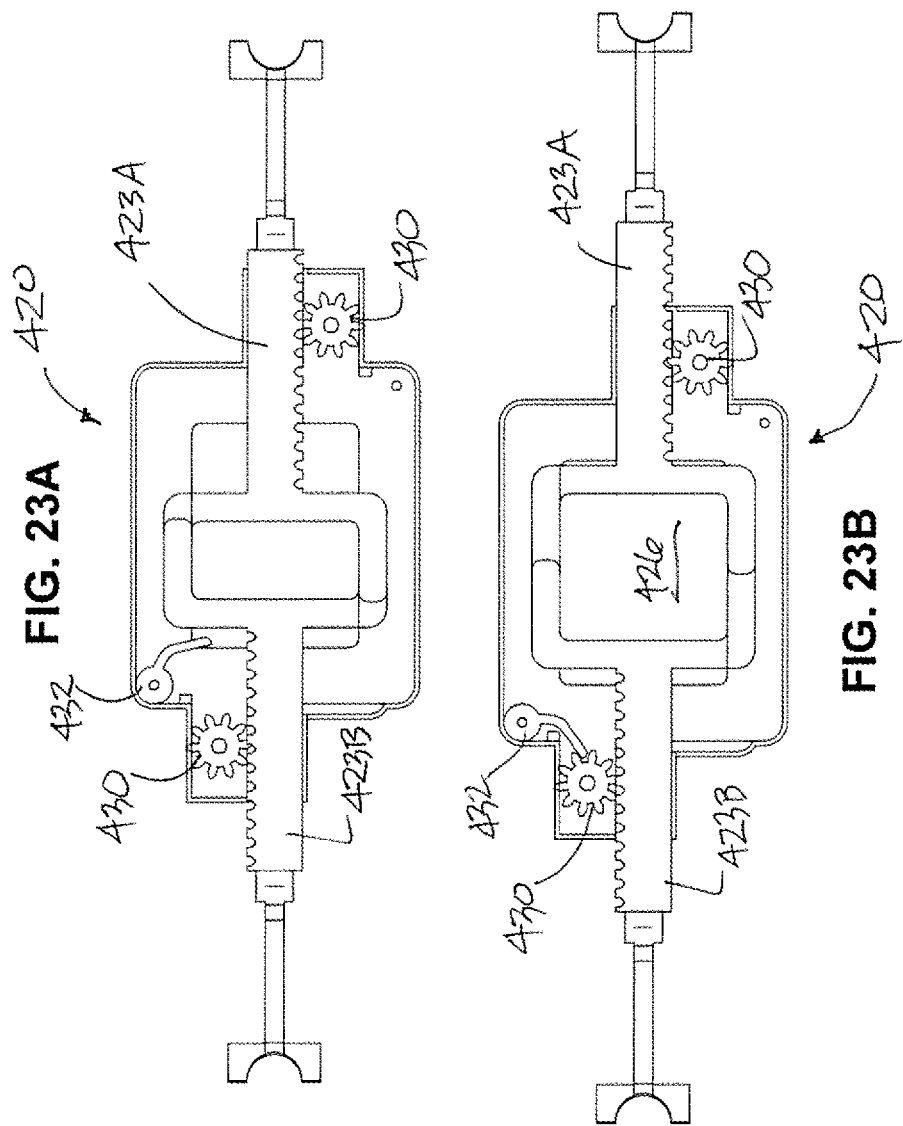

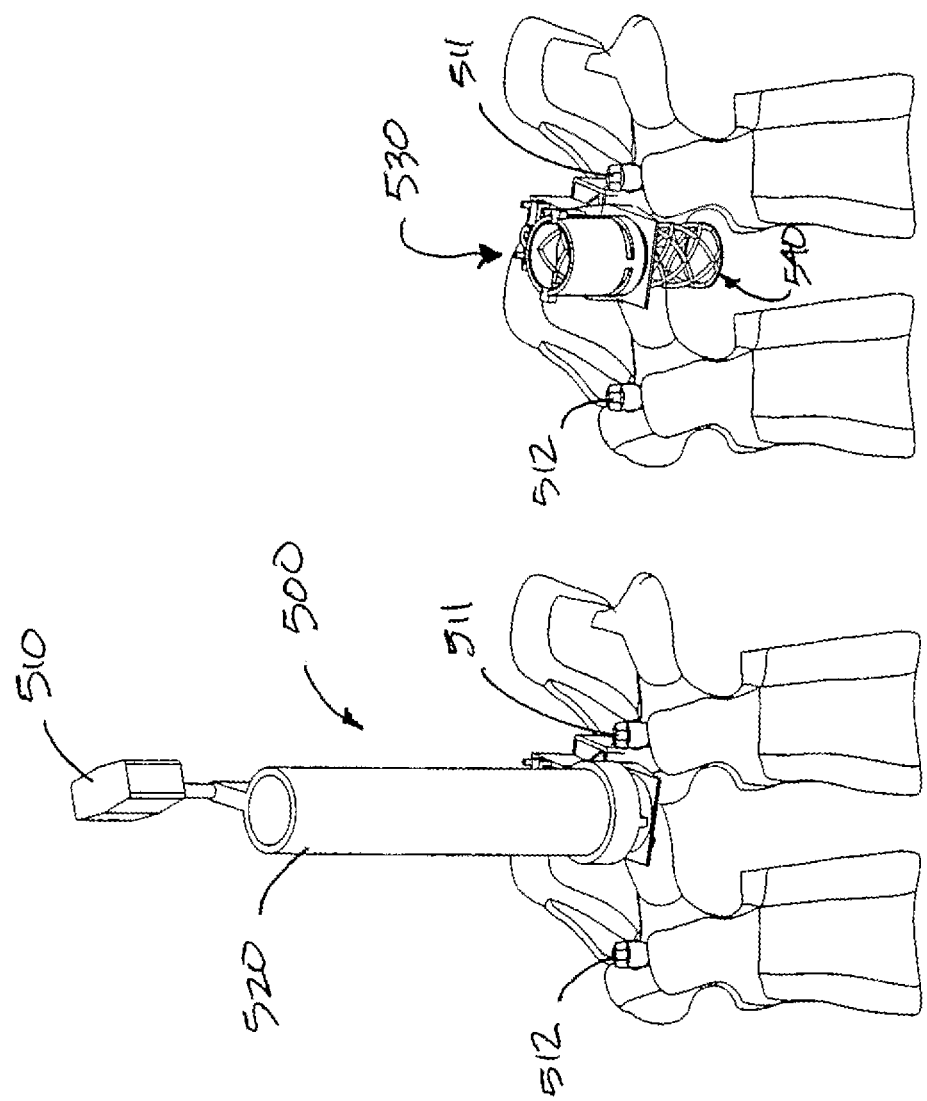

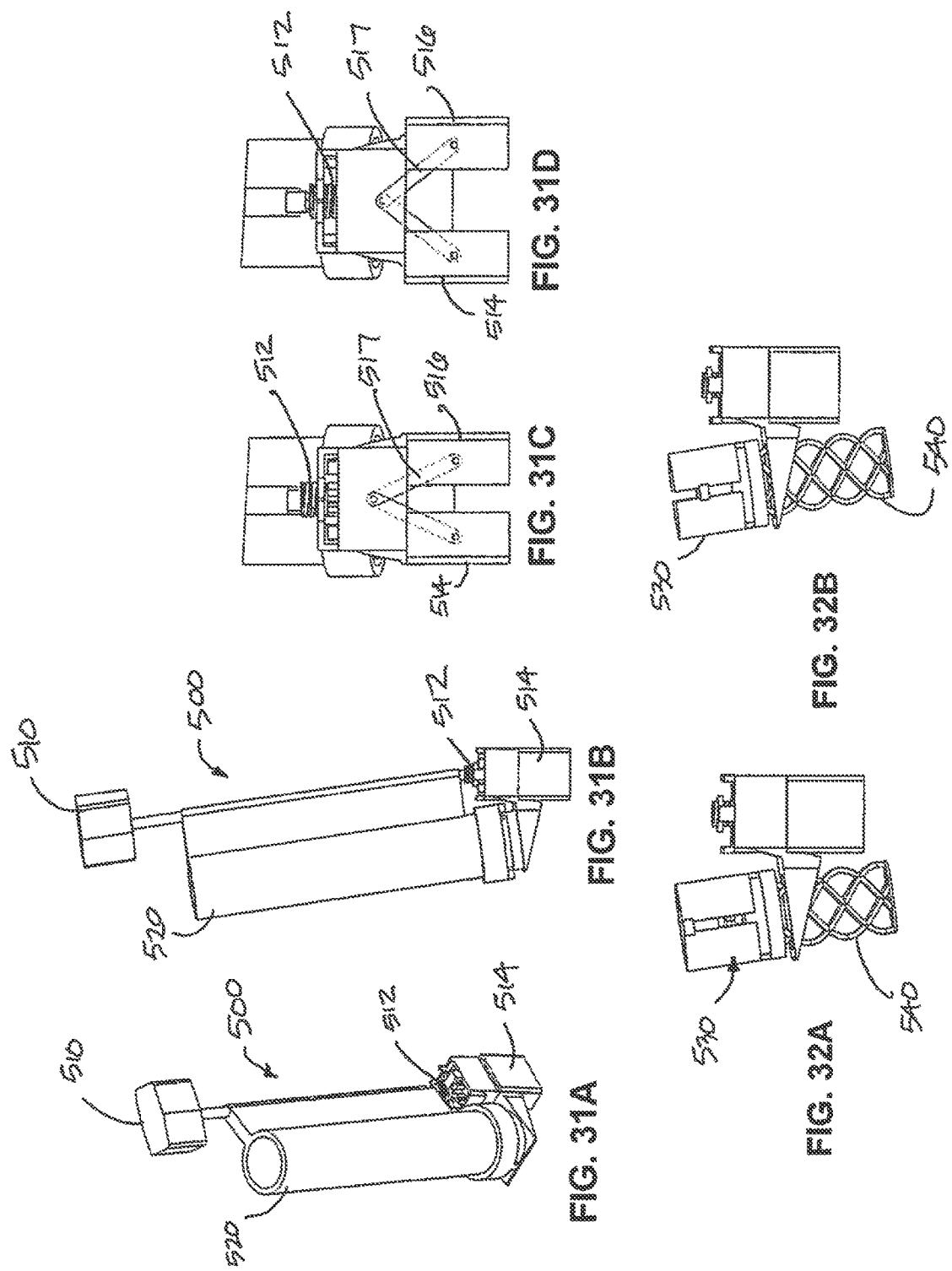

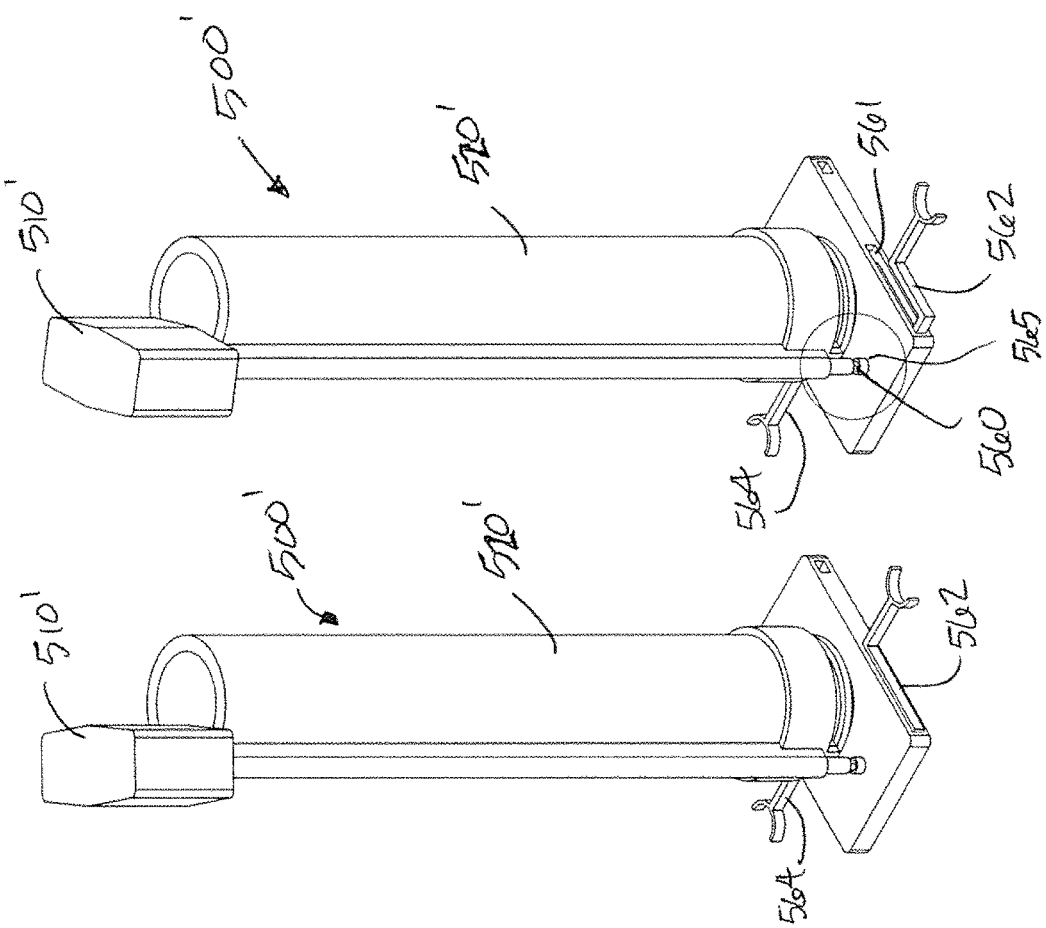
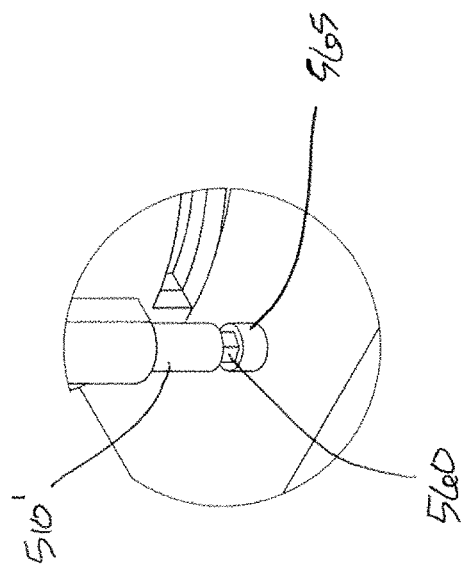

METHODS AND APPARATUS FOR INSERTION OF IMPLANT MATERIAL

CROSS-REFERENCE TO RELATED APPLICATIONS

This application is a continuation-in-part of U.S. patent application Ser. No. 12/434,328, filed May 1, 2009, which issued as U.S. Pat. No. 8,734,515 on May 27, 2014 and which in turn claims priority to provisional Application No. 61/051,036, filed on May 7, 2008, and which are both incorporated by reference herein in their entireties.

FIELD OF THE INVENTION

The invention relates to surgical implants, and more particularly to devices for distracting two or more anatomical features and/or inserting an implant material, and to methods related thereto.

BACKGROUND OF THE INVENTION

Currently, one of the most difficult portions of the human to repair and to protect during healing is the spinal column or spine. In simple terms, the spine may be viewed as a series of vertebrae connected by and alternating with intersticial positioned spinal discs. The spinal discs include an outer portion referred to as an annulus formed of relatively tough and only minimally elastic material that is, nonetheless, pliable and may be likened to leather. Each annulus surrounds a nucleus that is constituted from a highly viscous gel-type material. Each annulus is secured with a superior vertebra across a bony endplate of the vertebra, as well as an inferior vertebra across a bony endplate of the inferior vertebra.

Each vertebra has a channel for the spinal nerve separated from endplates and discs. The discs support and enable the biomechanical movement of the torso, such as flexion/extension in anterior, posterior, and lateral directions, and in torsional movement around a general vertical axis of the spine.

Should one or more discs be damaged, a person may experience pain from a number of the modes. In one mode, the annulus may be damaged so that the disc bulges and presses on the spinal nerve. In another mode, the annulus may fail to provide sufficient support so that the portion of the spine in a superior position to the damaged annulus compress downwardly, which also compresses the spinal nerve. Another mode is a damaged vertebra that results in pain or contributes to damage of portions of the spine.

A number of treatments are known for addressing spinal pain and other conditions (such as scoliosis or other unfortunate but naturally occurring conditions). While there are non-surgical treatments available for some pain originating from damage to the spinal column, such are typically limited to minor irregularities. For any significant damage, surgical procedures are often necessary to relieve pain and/or regain a portion of a person's mobility.

One category of such procedures is defined by the use of intervertebral implants. Intervertebral implants specifically are devices that are placed in the interstice that normally is occupied only by the naturally occurring spinal disc. Intervertebral implants may be total disc replacements (TDR) following a discectomy, removal of the entirety of the naturally occurring disc. Other intervertebral implants are intradiscal wherein a portion or entirety of the nucleus is removed (a procedure known as a nucleotomy) and replaced with one or more implants within the natural annulus. Some known implants designs, whether TDR or intradiscal, are designed to mimic or replace the natural biomechanical properties of the natural disc, while others are fusion discs seeking to immobilize the superior and inferior vertebrae, generally permanently. For fusion implants, it is known to design implants and perform procedures that seek to stimulate, promote, or benefit from bone in-growth into the intervertebral space, implants that may or may not include natural or artificial bone graft material.

There are a number of difficulties with current designs and procedures for locating and implanting the variety of intervertebral implants. To begin with, a common manner for implantation requires a distractor device applied to adjacent vertebrae. This is necessary, since the diseased disc space is typically very narrow, and collapsed. This disc space height must be restored if an optimal outcome is to be achieved. Replacing the support provided by the disc requires spanning the distance between the endplates, which have concave surfaces facing the disc. Therefore, the distance between the vertebrae at the outer portion of the nucleus is smaller than the desired height for the implant construct. Applying a distractor to the vertebrae assists in forcing the larger implant between the vertebrae.

One example of a prior art implantation device or insertion distractor is shown in U.S. Pat. No. 3,486,505, to Morrison. This '505 patent requires placing distal portions of opposed arms between adjacent vertebrae. Once there, a plunger or rod is advanced to force an implant between the arms, thereby spreading the arms and distal portions thereof outwardly to distract the vertebrae. This method and design puts a significant amount of stress on the implant itself, as it is the implant that is doing much of the work. Such compression may damage the implant before the implant is ever disposed in the intervertebral space, and high frictional forces are exerted on the sides of the implant that are in contact with the arms. Finally, as the implant is doing the work, manipulation of the implant to a desired purpose is hindered, particularly once the implant has passed beyond the arm distal portions so that it is in full and direct contact with the endplates.

While the design of the '505 needs the implant to slide, generally prevents use with an implant having surface fixation features such as spikes, U.S. Patent Application Publication No. 2008/0161817, to Parsons, et al. attempts to overcome such deficiency. Specifically, the implant has laterally located spikes, the arms of the inserter device engaging on a central portion of the implant with the spikes positioned outboard therefrom. Additionally, the plunger itself appears to provide at least a part of the distraction force for the arms. However, the '817 design maintains the spikes in an exposed position at all times during implantation. Additionally, the implant must be located between the arms at the distal end of the distractor/implantor device prior to placing the device in situ, resulting in the spikes being exposed and seating of the implant being susceptible to being effected during the preliminary steps of interfacing the distractor device with the vertebrae.

U.S. Pat. No. 6,368,325, to McKinley, et al., describes a distractor/implantor device specifically described for use with bone blocks. The device includes an elongated handle with a distal forked end defining a space for receiving a bone block therein. The leading surfaces of the fork tines are beveled and, in particular, are shown as having a bevel that aligns with a bevel surface formed on a leading end of the bone block protruding from between the tines. The bevel surfaces are used to initially wedge first the bone block, then the tines between the vertebrae, a major dimension extending laterally and a minor dimension extending in the spinal superior-inferior (rostral-caudal) direction. The entirety of the device is then rotated around its generally longitudinal axis to distract the vertebrae, the major axis being aligned with the superior-inferior direction. A central rod is then advanced to eject the bone block.

The design of the '325 patent overcomes some of the deficiencies of the above-discussed references, while still presenting other deficiencies. For instance, none of the devices permits selection of an implant device after distraction has occurred. A surgeon may desire to inspect and size the intradiscal or intervertebral space prior to selecting the implant. The above-discussed devices do not permit such inspection without sequential insertion and removal of the distractor/implantor device, or another device (such as a sizer or spacer). Similarly, none of the devices discussed herein allows for sequentially implanting a plurality of implant constructs, or components thereof. The '325 patent also relies on compression directly on the implant during insertion and rotation of the device. The major benefit of the design of the '325 patent is that, once the device is rotated and the vertebrae are distracted, the implant itself can relatively easily be advanced from the device without further distraction.

Another design for a distractor/implantor is illustrated by U.S. Patent Application Publication No. 2007/0270875, to Bacher, et al. Essentially, a central rod pointed tip is utilized as an initial distractor, an outer sleeve has fingers that form a frusto-conical portion extending from the rod pointed tip, and an inner sleeve receives the central rod while itself being received by the outer sleeve. While various uses of the illustrated device may be imagined, one minimally requires the inner and outer sleeves to remain between the vertebrae during distraction and implantation.

Accordingly, there has been a need for an improved distractor/implantor device for locating and implanting artificial spinal discs in intervertebral spaces.

SUMMARY OF THE INVENTION

In accordance with an aspect, a method of inserting implant material into an intervertebral space is disclosed including the steps of positioning a leading end of a surgical device between adjacent vertebrae in first orientation, the leading end having a first dimension aligned with a rostral-caudal direction and a second dimension larger than the first dimension and aligned in a lateral direction, rotating the leading end of the surgical device relative to the adjacent vertebrae to align the larger second dimension with the rostral-caudal direction and distract the adjacent vertebrae, loading the implant material into a cannula, wherein the implant material is not under compression during the step of rotating, and subsequent to the step of rotating, advancing the implant through the cannula and into the intervertebral space from the leading end.

In some forms, the step of positioning includes compressing the leading end in the rostral-caudal direction.

In some forms, the step of loading is prior to the step of positioning.

In some forms, the step of advancing the implant material includes expanding the leading end via force exerted by the implant material, the force received from an advancing rod.

In some forms, the method includes the step of selecting the implant material from one or more of fusion devices and bone graft material.

In some forms, the step of positioning includes determining a position of the surgical device by placing stops formed on the leading end against the adjacent vertebrae.

In some forms, the method further includes the step of preparing, wherein the step of preparing includes one or more of removing natural spinal disc material and determining geometrical features of the intervertebral space.

In an additional aspect, a surgical device for distraction and insertion of intevertebral implant material in an intervertebral space between adjacent vertebrae is disclosed including an elongated barrel, an operative end formed on a distally-located end of the barrel, the operative end for engaging the adjacent vertebrae, wherein the operative end includes a plurality of slots allowing at least the operative end to be expanded, and includes a major dimension and a minor dimension, a cannula leading from a proximally-located portion of the barrel to an opening thereof, the opening at the operative end for disposing of the implant material therefrom, wherein the operative end minor dimension is sized to be received between the adjacent vertebrae in an initial insertion, the major dimension is sized for distracting the adjacent vertebrae to permit the implant material to be disposed thereinto, the vertebrae being distracted by rotation of the operative end after the initial insertion, and the implant material is retained within the cannula without significant compression during rotation of the operative end.

In some forms, the surgical device further includes a loading chamber for loading of the implant material into the cannula and a reciprocable rod disposed at least partially in the cannula for advancing the implant material therethrough and from the opening. The cannula may have a non-uniform size such that the cannula is smaller at the opening. The implant material may be advanced through the opening to expand the operative end. The implant material may be advanced through the opening to at least partially distract the adjacent vertebrae.

In some forms, the rod may be advanced by actuation of a trigger, rotating knob, or other actuator, operatively connected to the rod.

In another aspect, a surgical device for distraction and insertion of intevertebral implant material in an intervertebral space between adjacent vertebrae is disclosed including an elongated barrel, an operative end formed on a distally-located end of the barrel, the operative end for engaging the adjacent vertebrae, wherein the operative end includes a plurality of slots allowing at least the operative end to be expanded, and includes a rostral-caudal dimension and a lateral dimension, wherein the operative end rostral-caudal dimension is sized to be received between the adjacent vertebrae in an initial insertion, a cannula leading from a proximally-located portion of the barrel to an opening thereof, the opening at the operative end for disposing of the implant material therefrom, and an inner member reciprocable within the barrel and having features located thereon for engaging surfaces of the slots of the barrel, movement of the features against the surfaces expanding the barrel and distracting adjacent vertebrae when the operative end is located thereat.

In some forms, the slots are angled, and the inner member features are wedge-shaped for contacting the angled slots. Refraction of the inner member in a direction away from the operative end may forces the wedges through the slots to expand the barrel in the rostral-caudal dimension.

In some forms, surgical device may include stops for maintaining the features in the desired position along the slots.

In some forms, the surgical device further includes a loading chamber for loading of the implant material into the cannula, and including a reciprocable rod disposed at least partially in the cannula for advancing the implant material therethrough and from the opening.

In some forms, the implant material may be advanced through the opening to at least partially distract the adjacent vertebrae.

In some forms, the rod may be advanced by actuation of a trigger, rotating knob, or other actuator, operatively connected to the rod.

In some embodiments, the surgical device comprises a component for mating and/or docking against one or more anatomical features of a patient.

In some embodiments, the surgical device comprises a cam mechanism that permits a user to at least partially distract adjacent vertebrae.

In some embodiments, the surgical device comprises a barrel that permits a user to at least partially distract patient tissue and/or dilate the barrel for use of the surgical device in a minimally invasive surgical procedure.

Other embodiments and aspect of the present disclosure will be understood after reviewing the accompanying specification and appended drawing figures.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

In the drawings:

FIG. 1 is a side elevational view of a first form of a surgical device for distracting adjacent vertebrae and inserting an intervertebral disc implant into an intervertebral space between the adjacent vertebrae, the device including an advancable rod for directing the implant received in a loading chamber through a cannula of the device, the rod being shown as broken to indicate length;

FIG. 2 is a cross-sectional view taken through the line 2-2 of FIG. 1 showing the profile of an operative end portion of a barrel of the surgical device, the device having been rotated 90 degrees from the first orientation of FIG. 1 to the second orientation of FIG. 2;

Figure 3:
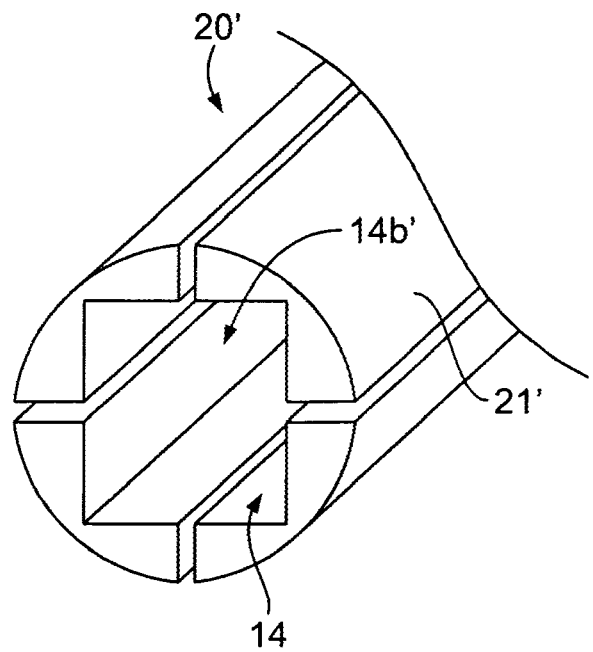
Figure 4:
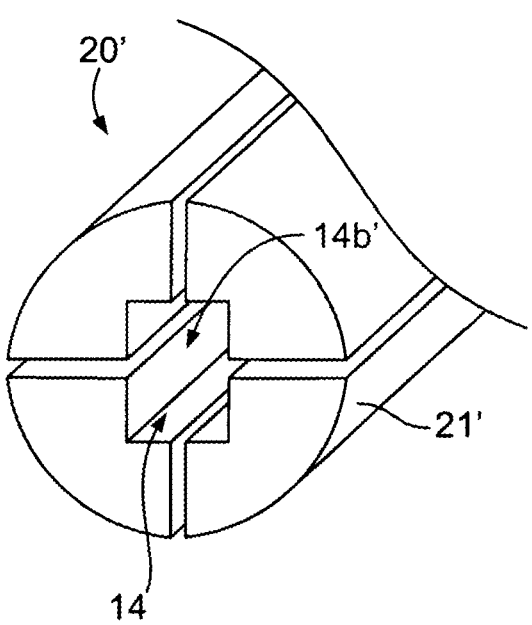
Figure 6:
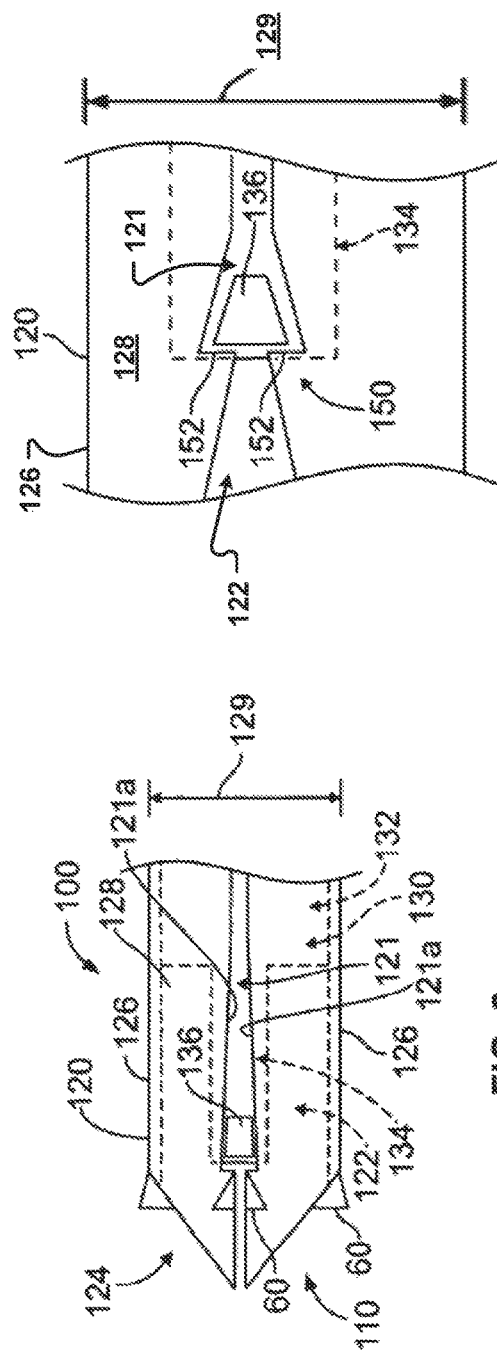
Figure 7:
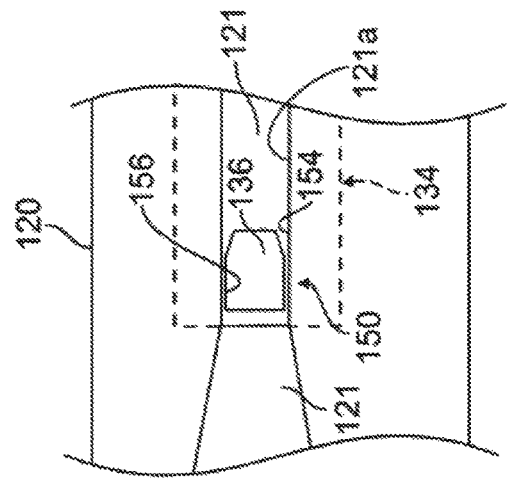
Figure 8:
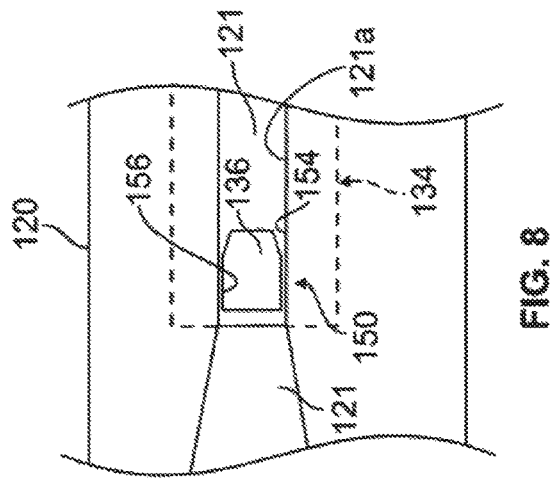
Figure 6A:
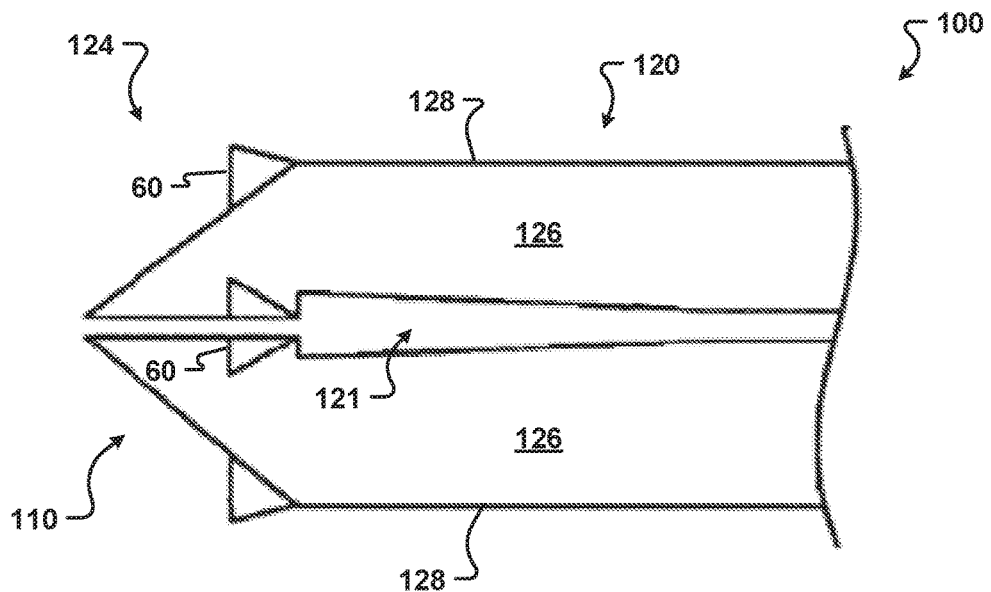
Figure 6B:
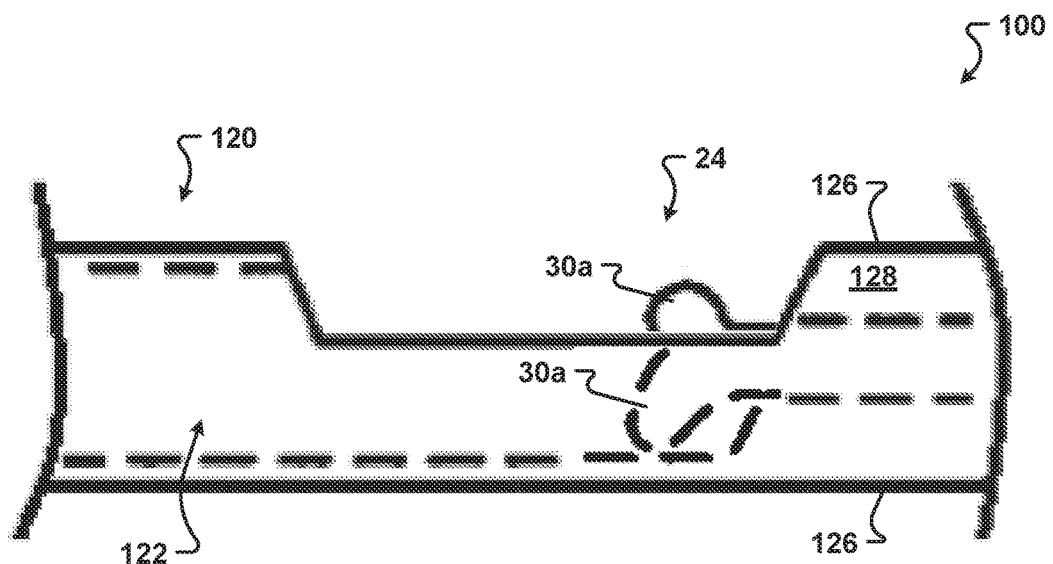
Figure 10A:
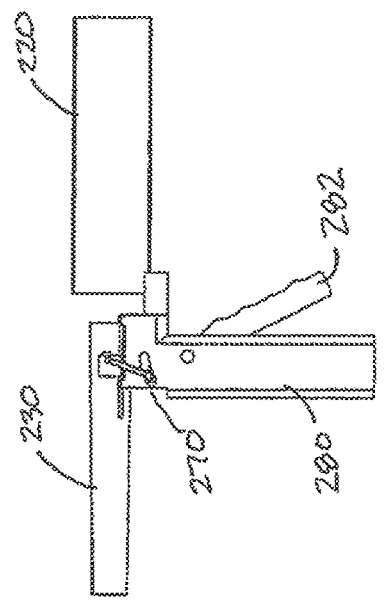
Figure 10B:
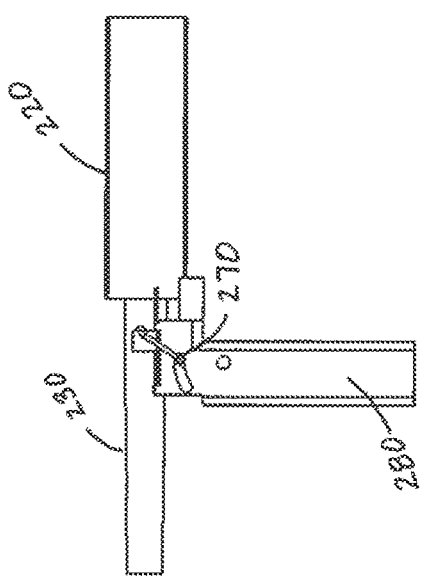
Figure 10C:
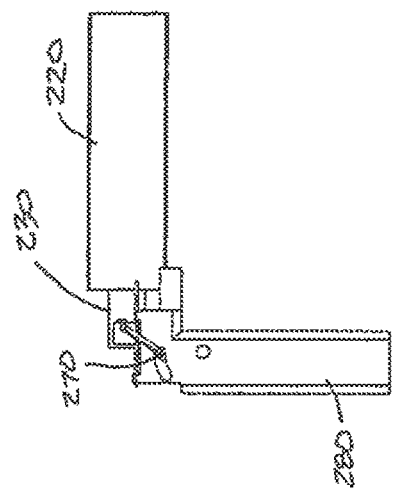
Figure 10D:
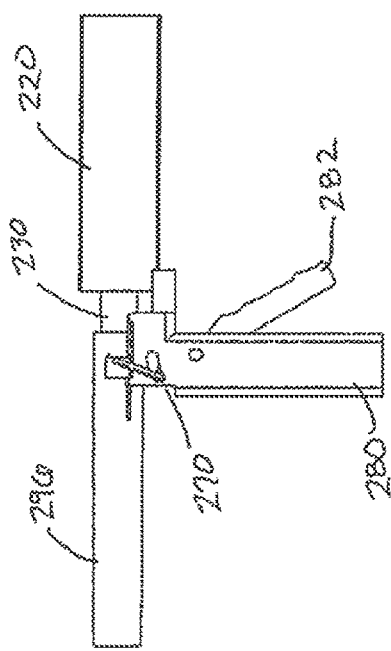
Figure 14:
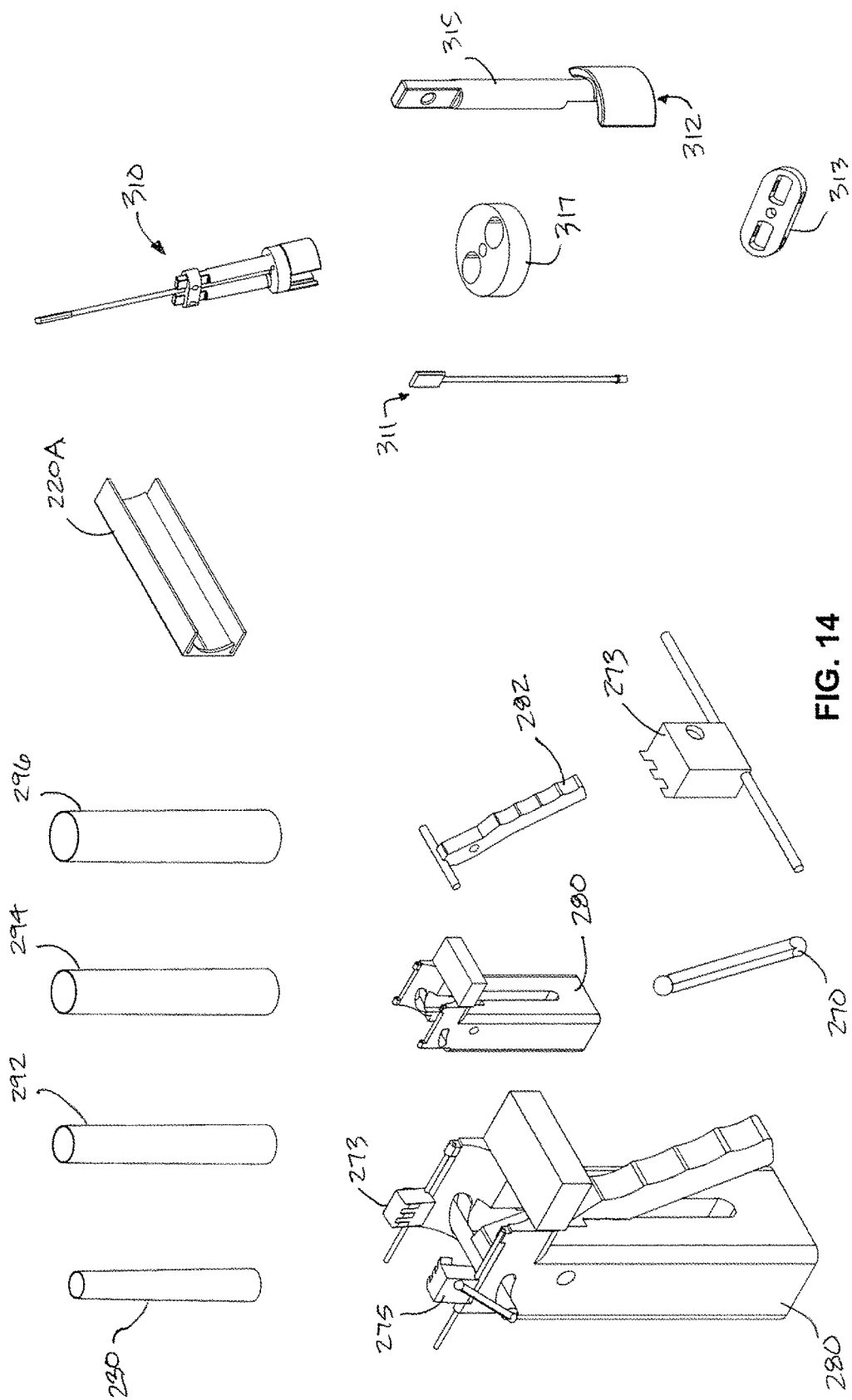
Figure 15:
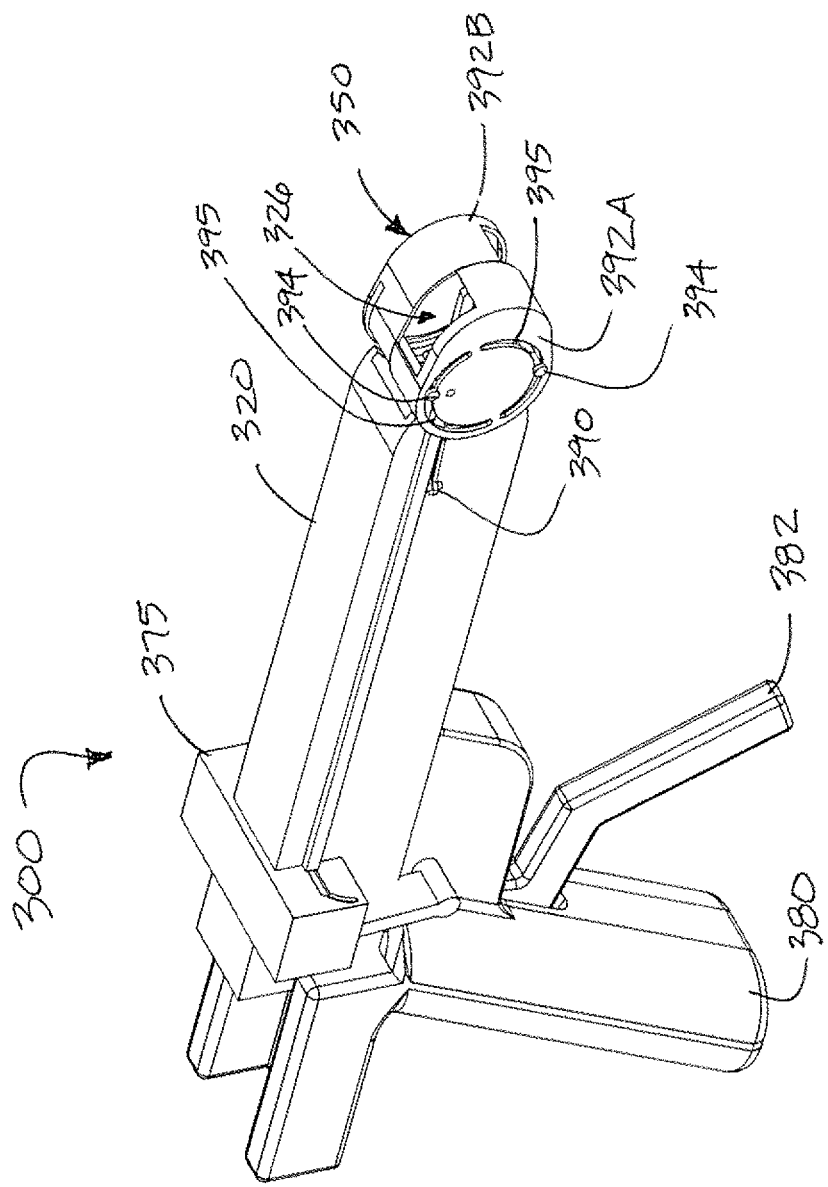
Figure 18C:
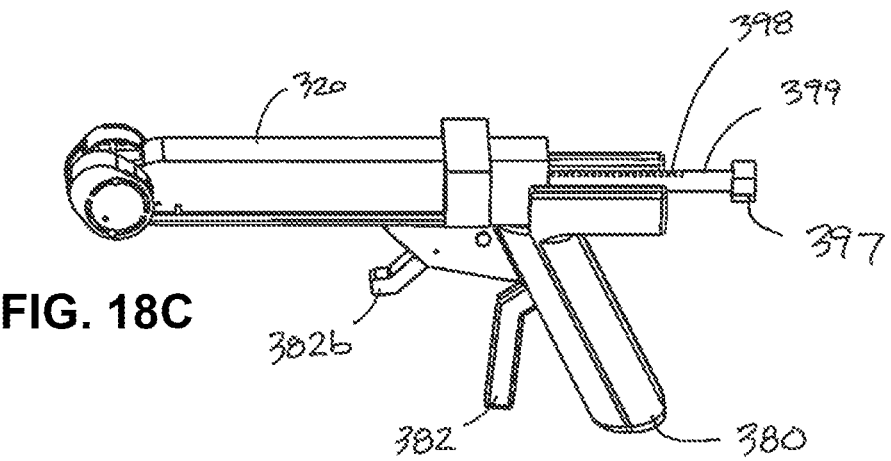
Figure 18D:
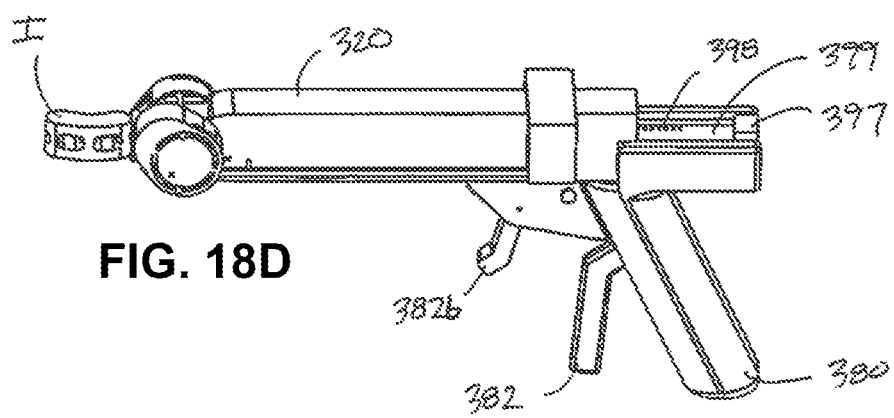
Figure 18E:
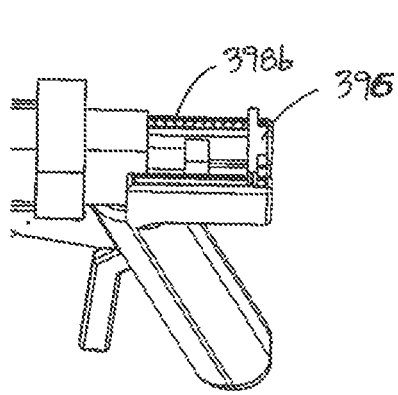
Figure 18F:
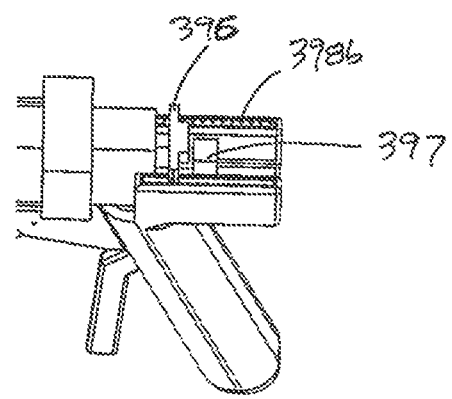
Figure 18G:
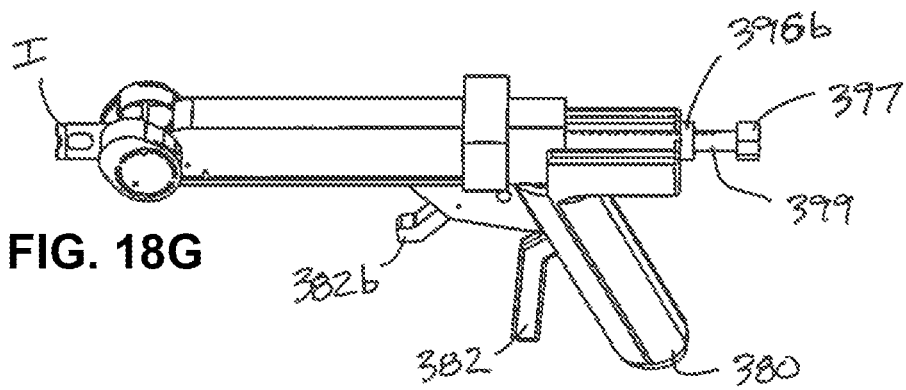
Figure 18H:
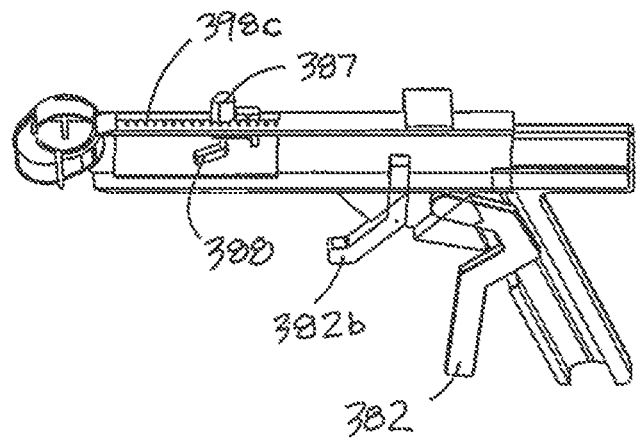
Figure 18I:
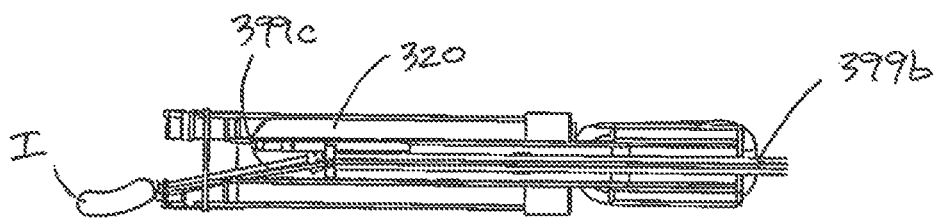
Figure 18J:
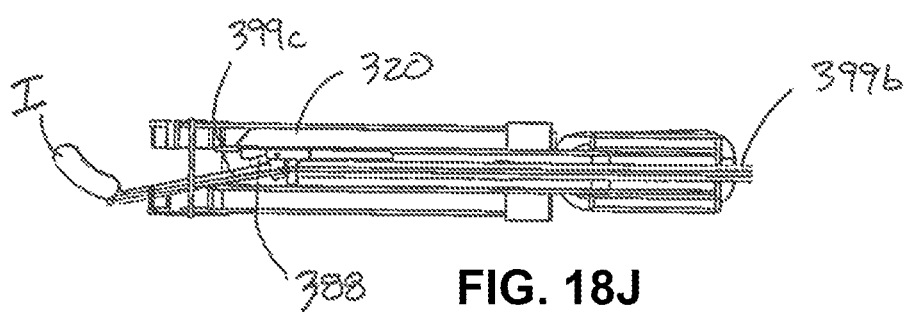
Figure 19:
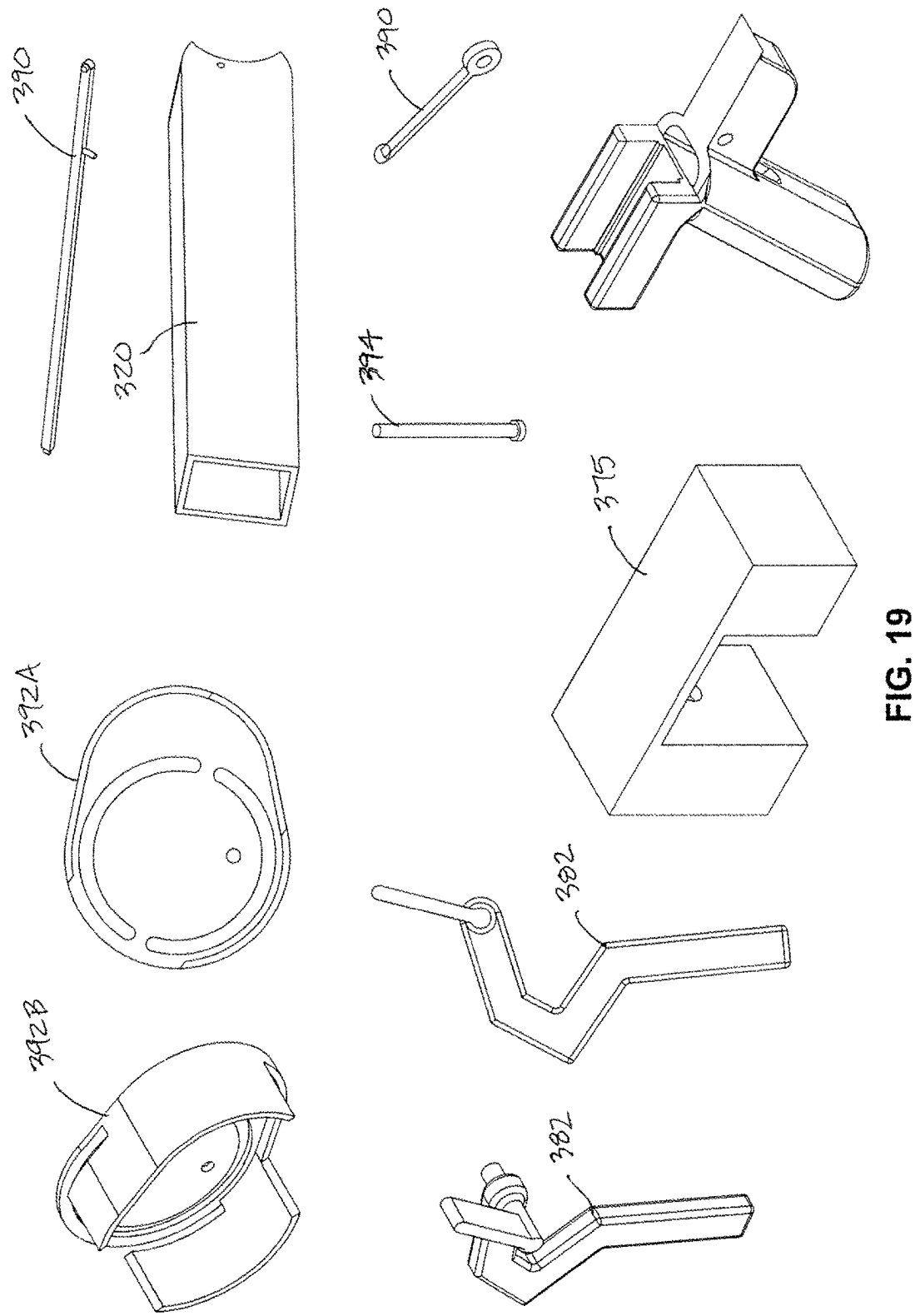
Figure 21C:
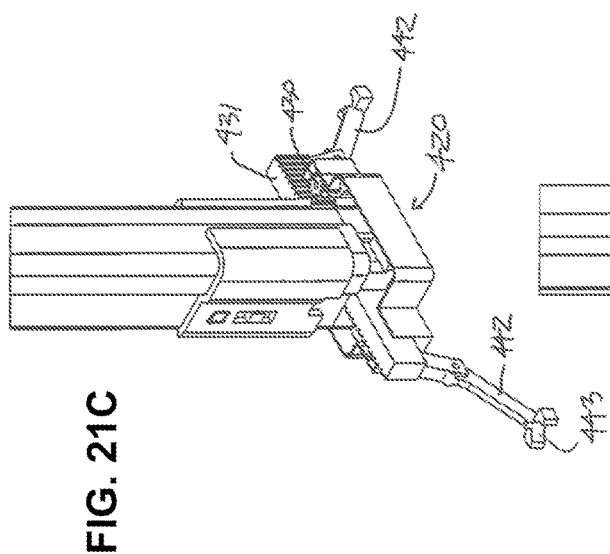
Figure 21D:
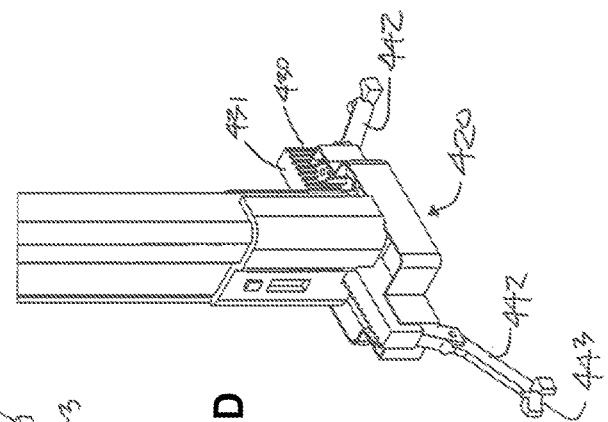
Figure 21B:
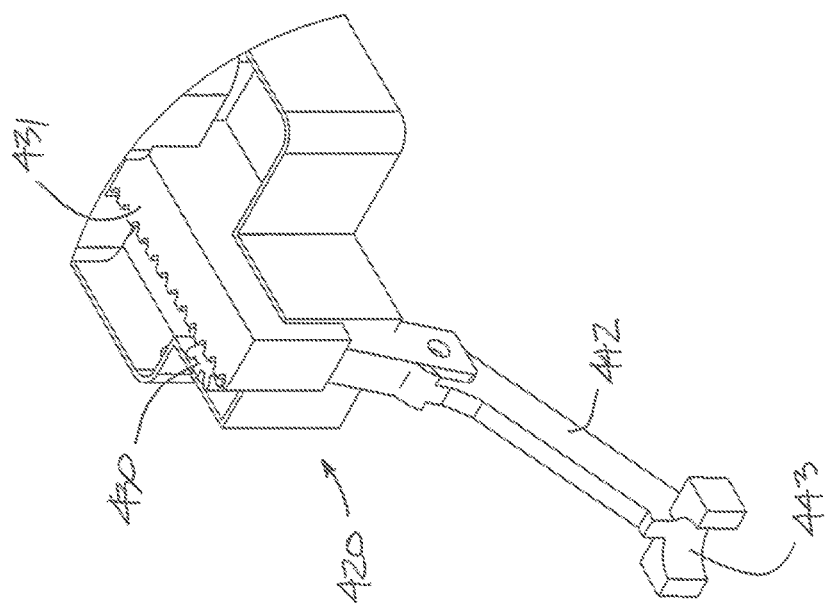
Figure 21A:
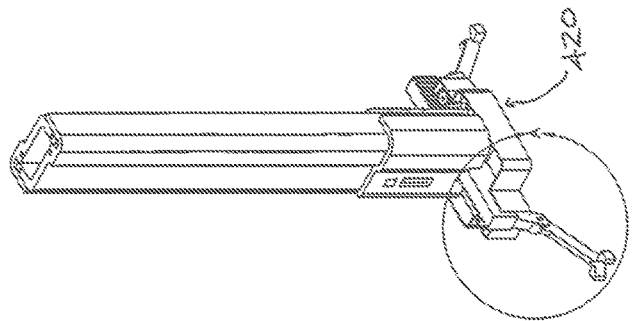
Figure 24:
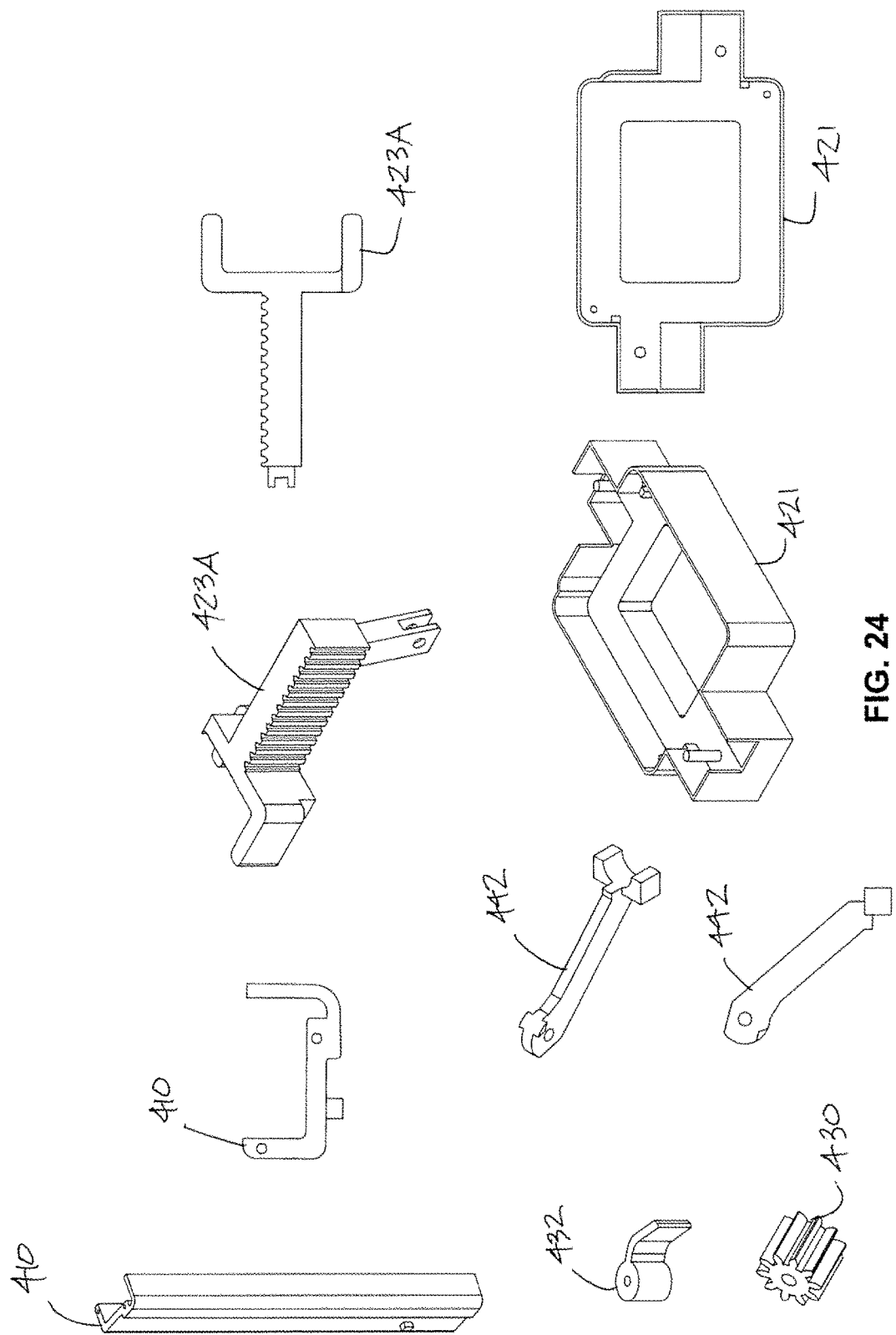
Figure 25B:
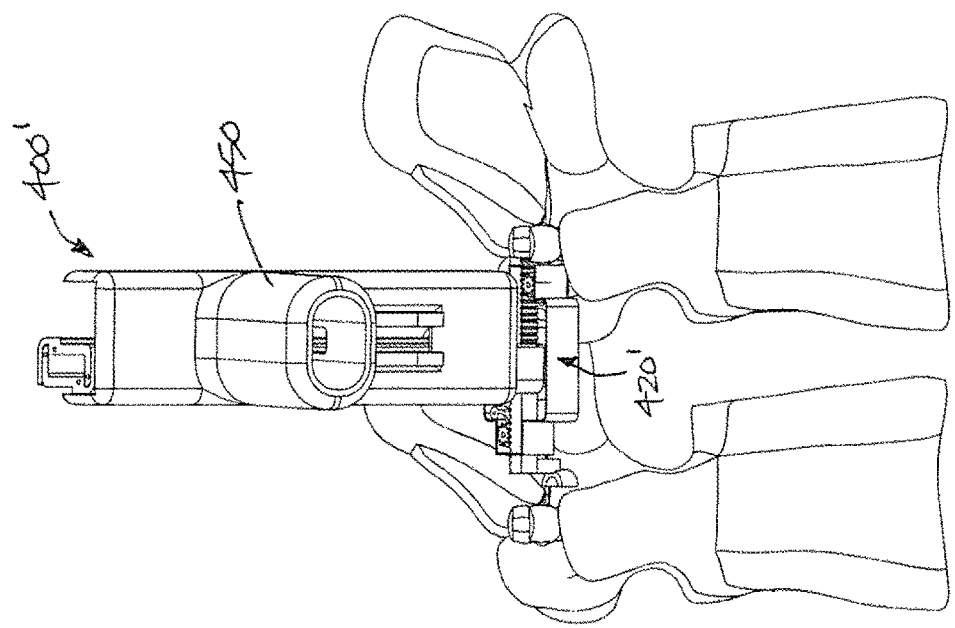
Figure 25A:
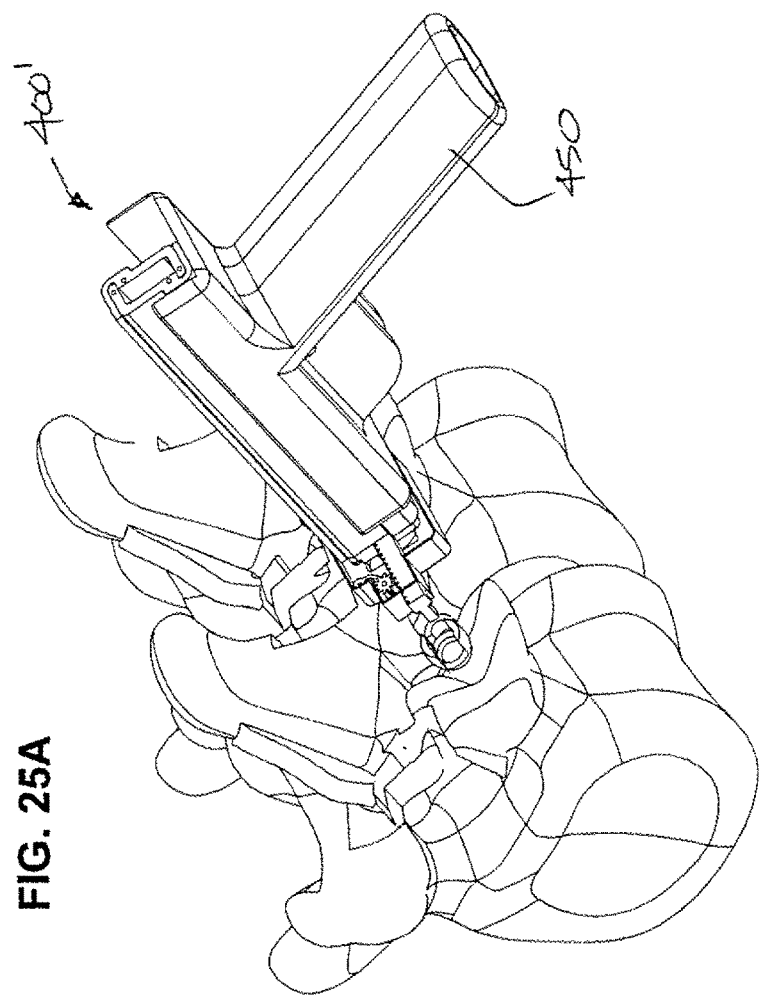
Figure 26C:
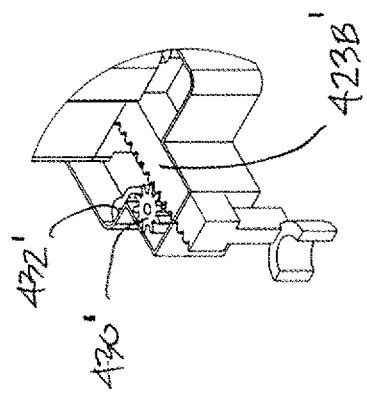
Figure 26B:
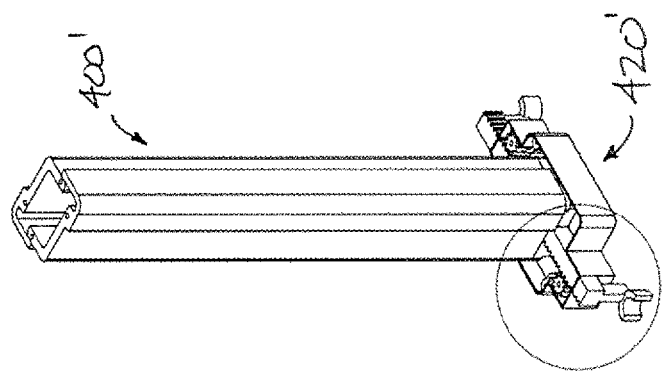
Figure 26A:
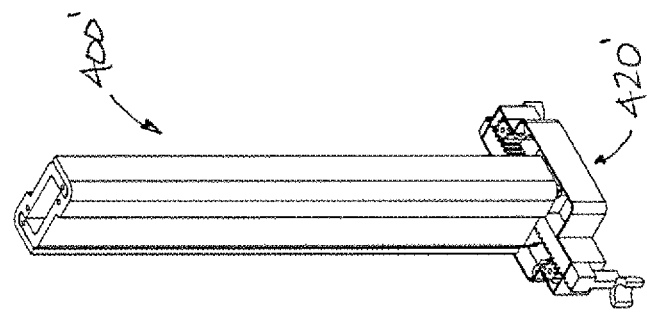
Figure 27C:
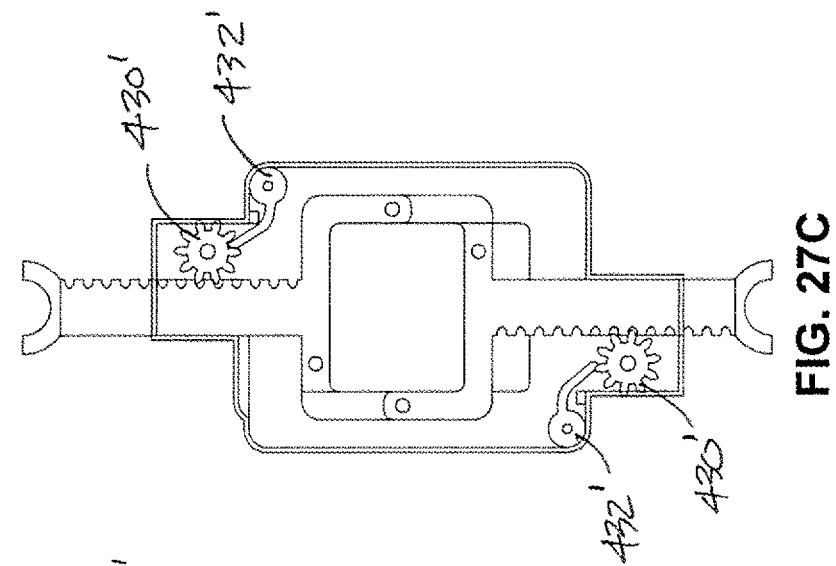
Figure 27B:
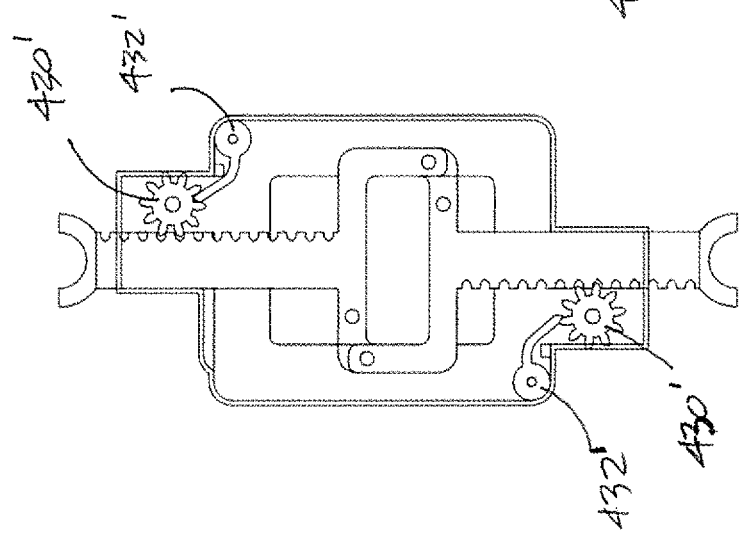
Figure 27A:
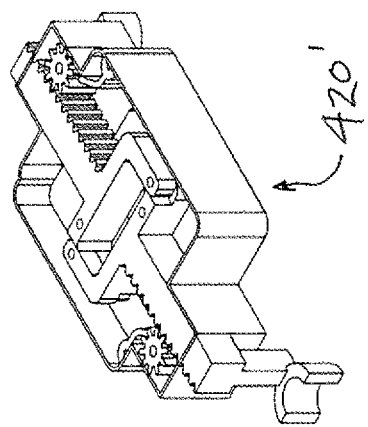
Figure 28:
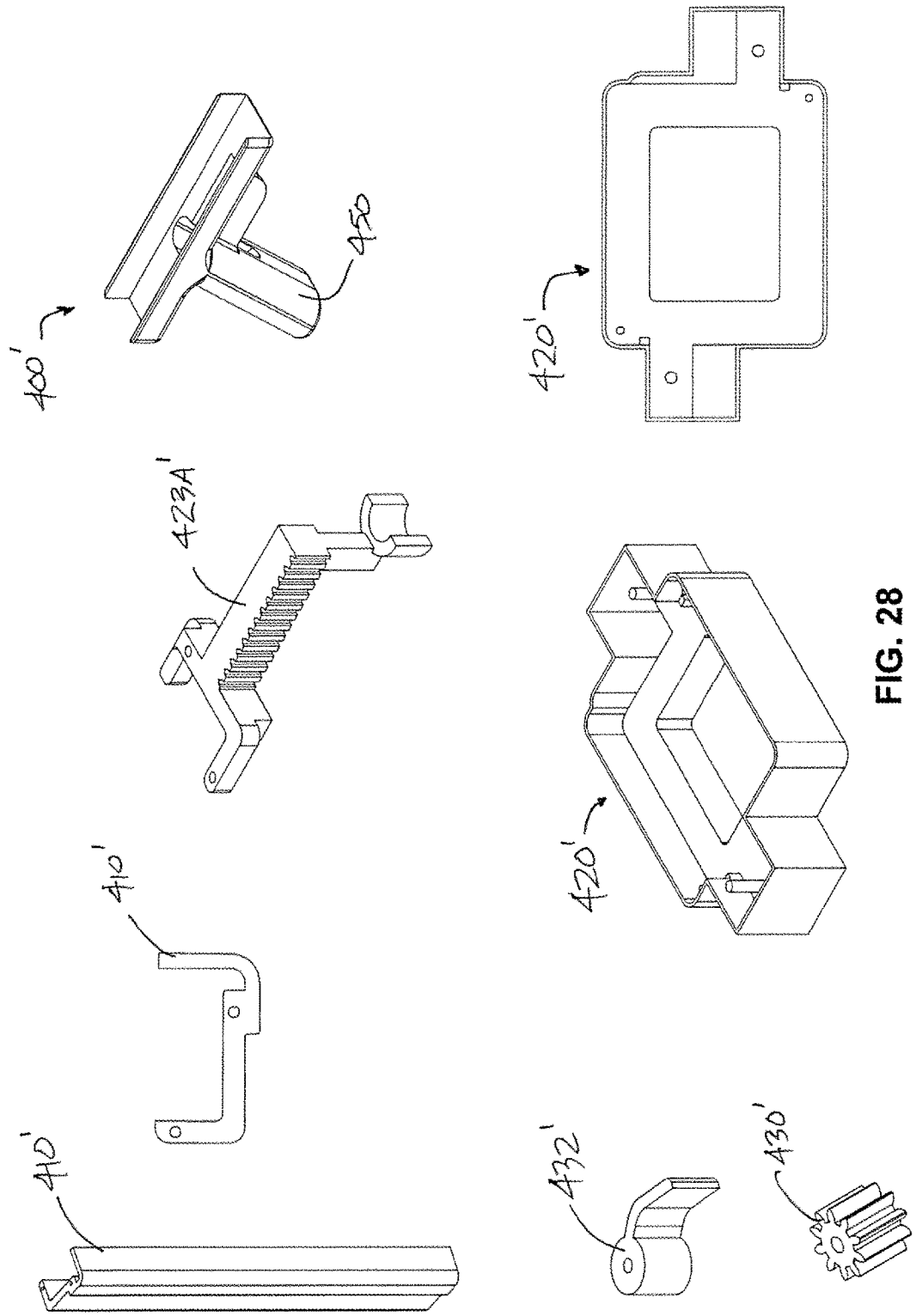
Figure 29B:
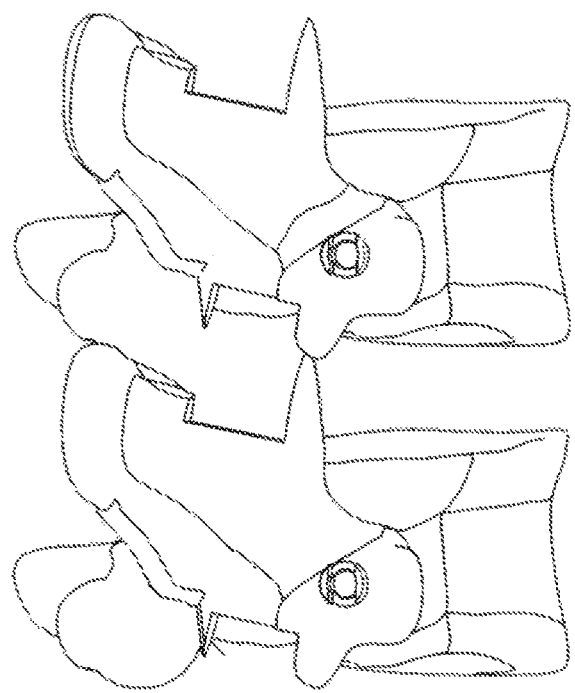
Figure 29A:
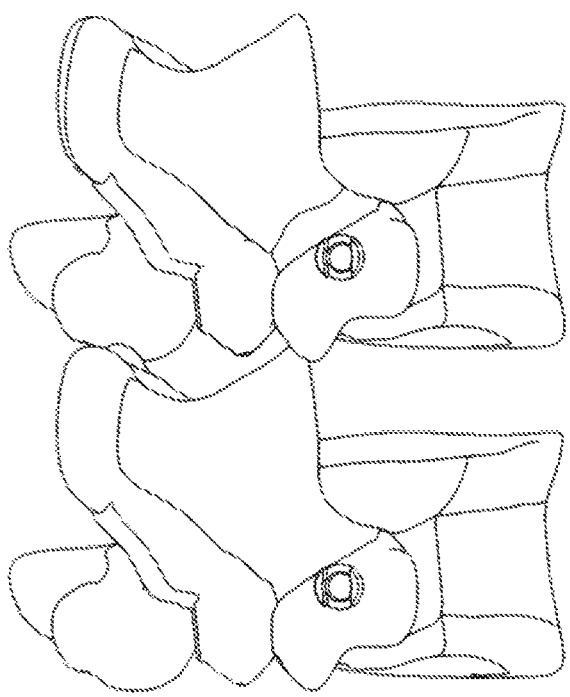

FIGS. 3 and 4 are enlarged fragmentary views of an alternate barrel for the device showing an inner cannula, FIG. 3 showing the cannula having larger dimensions than the cannula shown in FIG. 4, the large dimension portion of FIG. 3 being positioned within the device more rearwardly than the smaller dimension portion of FIG. 4 so that advancement of a rigid implant therethrough expands the barrel via the illustrated slots;

FIG. 5 is an enlarged fragmentary view of the operative end of FIG. 1 showing a sheath or skirt, comprised of a stretchable, or elastomeric material, disposed thereon for protecting surrounding tissues;

FIG. 6 is an enlarged fragmentary side elevation view of a barrel of a second form of a surgical device, the barrel having slots cooperating with a wedges formed on a second member to expand the slots and the barrel when the second member is retracted;

FIG. 6A is an enlarged fragmentary top plan view of the barrel of the surgical device of FIG. 6;

FIG. 6B is an enlarged fragmentary side elevation view of a portion of the barrel of the surgical device of FIG. 6 and further illustrating a loading chamber;

FIG. 7 is an enlarged fragmentary view of a portion of a form of the barrel and second member of FIG. 6 the showing a stop for receiving the wedge, the stop formed on the slot;

FIG. 8 is an enlarged fragmentary view of a portion of a form of the barrel and second member of FIG. 6 showing a stop, the stop formed on and between the slot and the wedge;

FIG. 9A shows a side perspective view of a surgical device according to one embodiment of the present disclosure;

FIG. 9B is a front perspective view of the surgical device of FIG. 9A;

FIG. 10A shows the surgical device of FIG. 9A in a first operative position;

FIG. 10B shows the surgical device of FIG. 9A in an intermediate operative position FIG. 10C shows the surgical device of FIG. 9A in a second operative position FIG. 10D shows the surgical device of FIG. 9A including the devices of FIG. 11A;

FIG. 11A shows a side elevation view of dilation rods for use with the surgical device of FIG. 9A;

FIG. 11B is another side elevation view of the surgical device of FIG. 9A and the dilation rods of FIG. 11A;

FIG. 11C is a front elevation view of the surgical device of FIG. 11B;

FIG. 12 is a side elevation view of the surgical device of FIG. 9A including the device of FIG. 13A FIG. 13A is a top elevation view of an access portal according to one embodiment of the present disclosure;

FIG. 13B is a front perceptive view of the access portal of FIG. 13A;

FIG. 14 is a view of various components described in relation to FIGS. 9A through 13B in an unassembled state;

FIG. 15 is a front perspective view of a surgical device according to yet another embodiment of the present disclosure;

FIG. 16A is a side elevation view of the surgical device of FIG. 15;

FIG. 16B is a detailed view of the surgical device of FIG. 16A;

FIG. 16C shows the surgical device of FIG. 16A in a second position;

FIG. 16D shows a detailed view of the surgical device of FIG. 16C;

FIG. 17A is a top plan view of the surgical device of FIG. 15;

FIG. 17B is a top plan view of the surgical device of FIG. 15;

FIG. 17C is a front elevation view of the surgical device of FIG. 15, corresponding to a second position as shown in FIG. 16C;

FIG. 17D is a detailed, front elevation view of the surgical device of FIG. 17C;

FIG. 18A is a side perspective view of the surgical device of FIG. 15 including an implant material and implant material insertion instrument;

FIG. 18B is a side elevation view of the surgical device of FIG. 18A in a second position;

FIGS. 18C-D are side perspective views of the surgical device according to another embodiment of the present disclosure;

FIGS. 18E-F are detailed top perspective views of the surgical device according to another embodiment of the present disclosure;

FIGS. 18G-J are various views of the surgical device according to yet another embodiment of the present disclosure;

FIGS. 18K-N are perspective views of an insertion rod for use with the surgical devices according to one embodiment of the present disclosure;

FIG. 19 is a view of various components described in relation to FIGS. 15 through 18B in an unassembled state;

FIG. 20A is a side perspective view of a surgical device according to yet another embodiment of the present disclosure;

FIG. 20B is a front perspective view of the surgical device of FIG. 20A;

FIG. 21A is a side perspective view of the surgical device of FIG. 20A;

FIG. 21B is a detailed view of the surgical device of FIG. 21A;

FIG. 21C is a side perspective view of the surgical device of FIG. 21A in a first position;

FIG. 21D is a side perspective view of the surgical device of FIG. 21A in a second position;

FIG. 22A shows a front perspective view of the ratcheting mechanism of the surgical device of FIG. 20A;

FIG. 22B shows a front elevation view of the ratcheting mechanism of the surgical device of FIG. 20A in a first position;

FIG. 22C shows a front elevation view of the ratcheting mechanism of the surgical device of FIG. 20A in a second position;

FIG. 23A shows the ratcheting mechanism of FIG. 22A in a first position;

FIG. 23B shows the ratcheting mechanism of FIG. 22A in a second position;

FIG. 24 is a view of various components described in relation to FIGS. 20A through 23B in an unassembled state;

FIG. 25A is a side perspective view of a surgical device according to yet another embodiment of the present disclosure;

FIG. 25B is a rear elevation view of the surgical device of FIG. 25A;

FIG. 26A is a side perspective view of the surgical device of FIG. 25A;

FIG. 26B is another side perspective view of the surgical device of FIG. 25A;

FIG. 26C is a detailed view of the ratcheting mechanism of the surgical device of FIG. 25A;

FIGS. 27A-C show partially exploded views of the ratcheting mechanism of FIG. 26C;

FIG. 28 is a view of various components described in relation to FIGS. 25A through 27C in an unassembled state;

FIG. 29A is a perspective view of a surgical site for use with the surgical device of FIGS. 30-34;

FIG. 29B is a perspective view of the surgical site of FIG. 29A with a portion of the boney anatomy dissected to permit insertion of the surgical device of FIGS. 30-34.

Figure 33B:
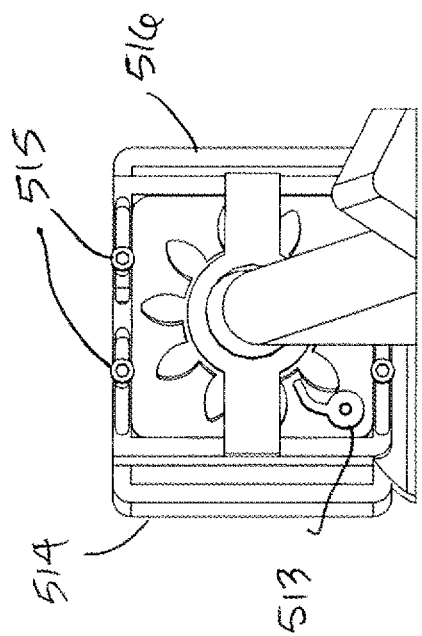
Figure 33A:
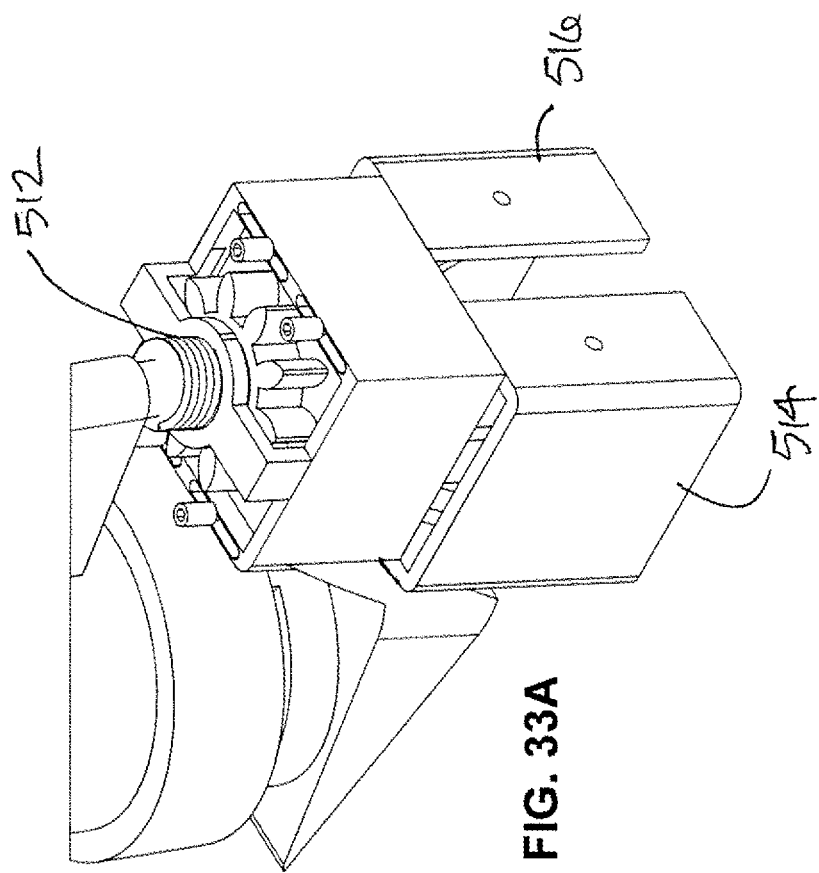
Figure 34:
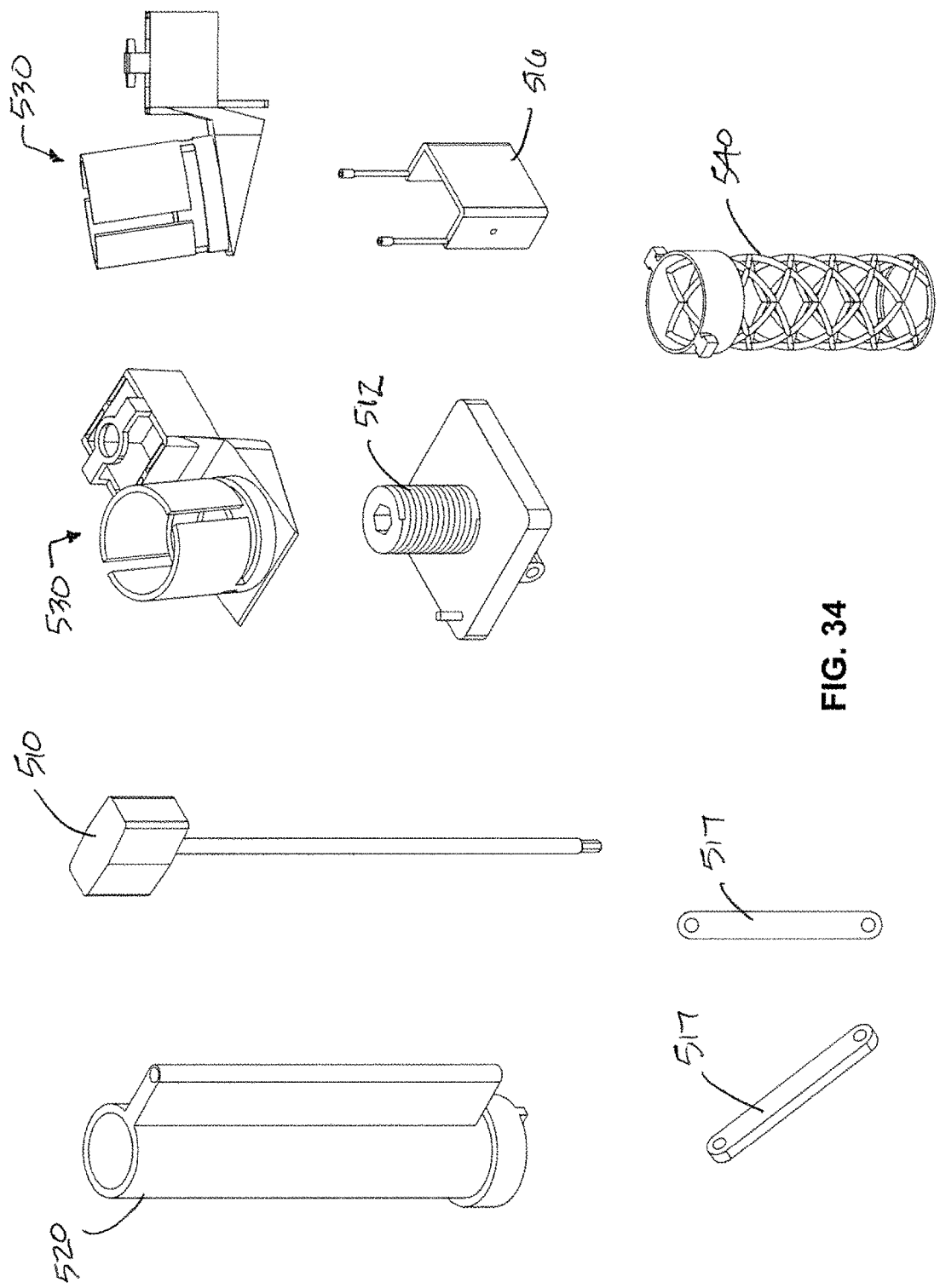
Figure 35A:
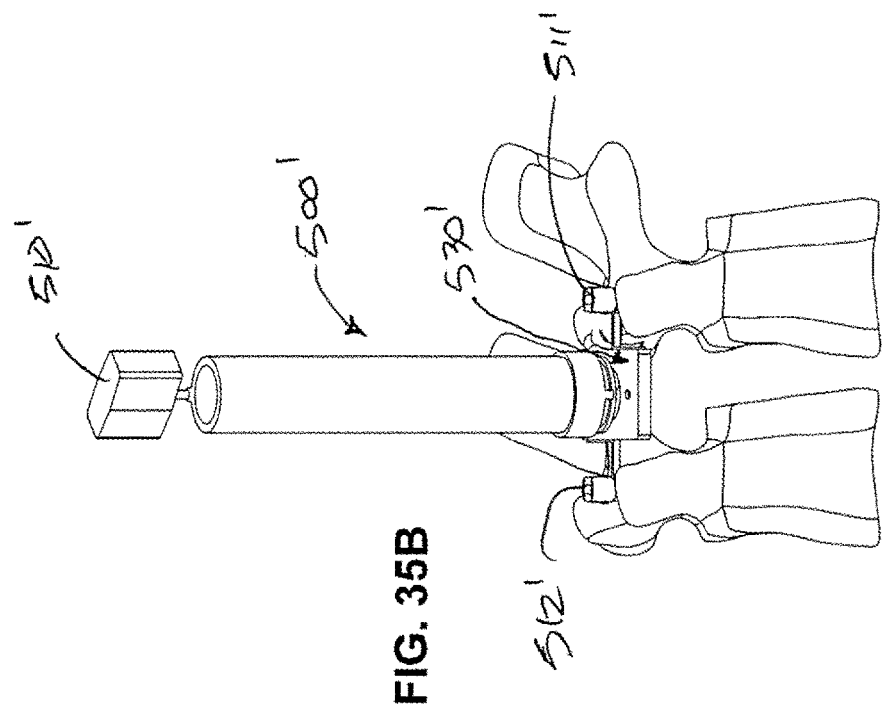
Figure 35B:
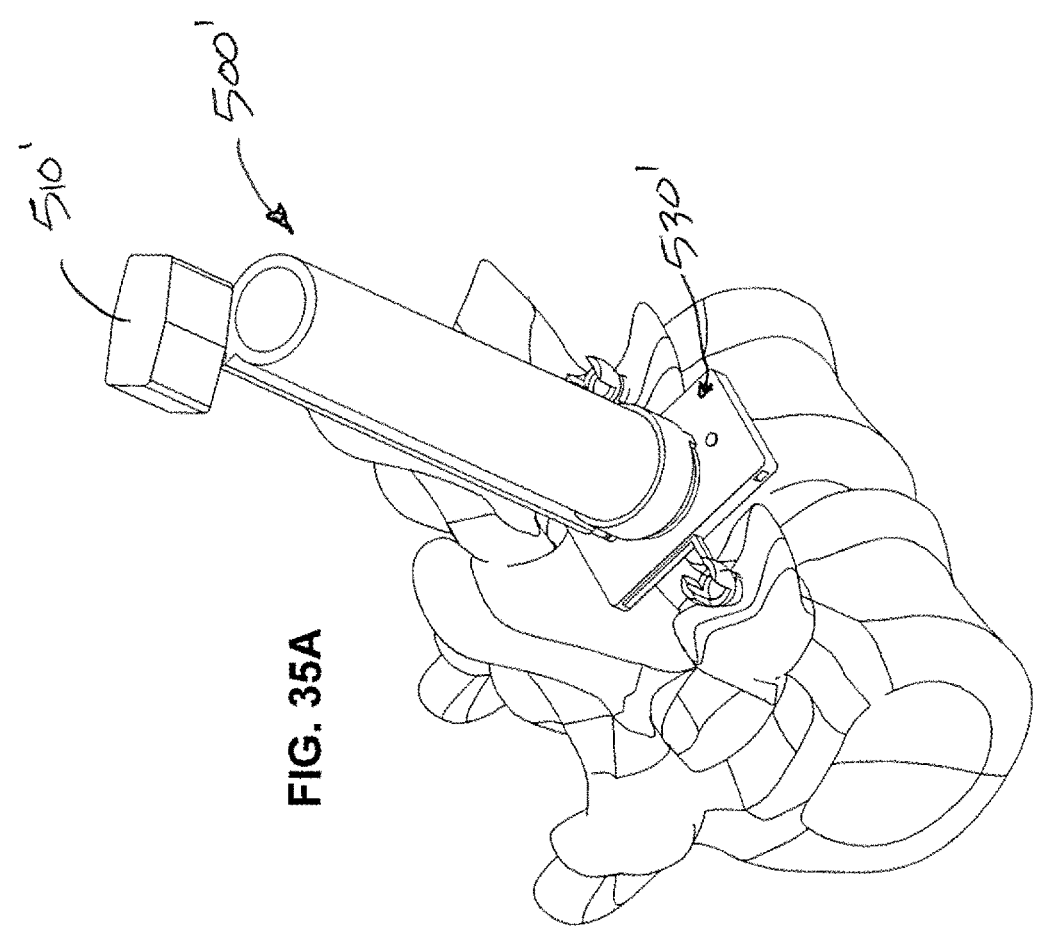
Figures 37A, 37B, 37C:
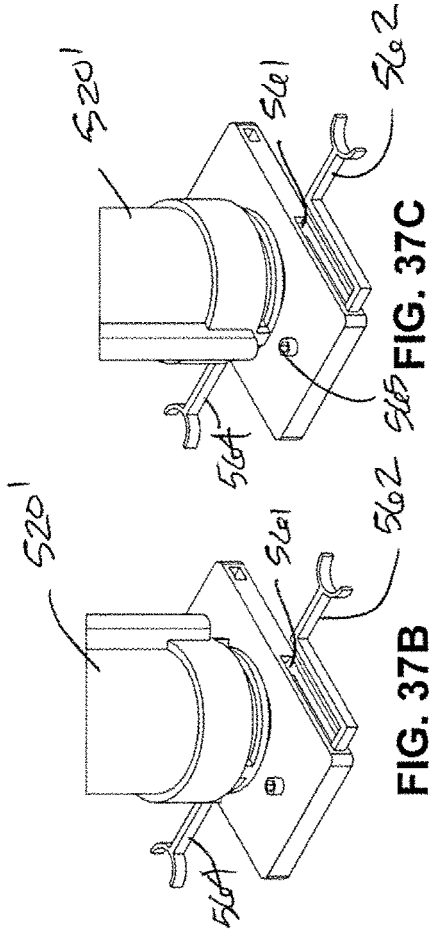
Figure 37D:
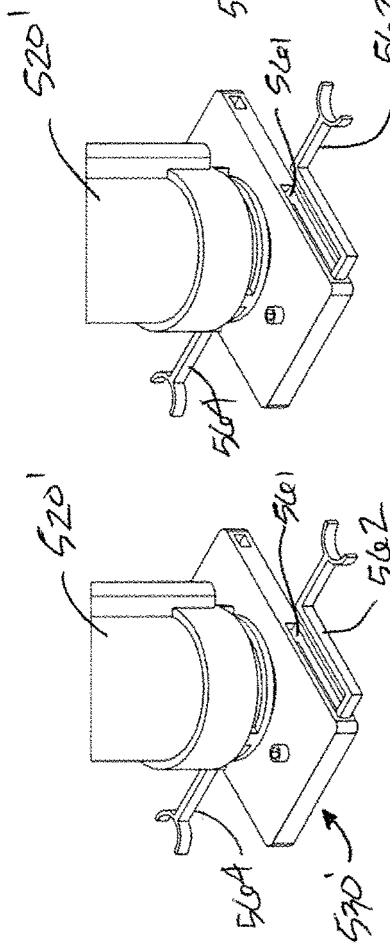
Figure 37E:
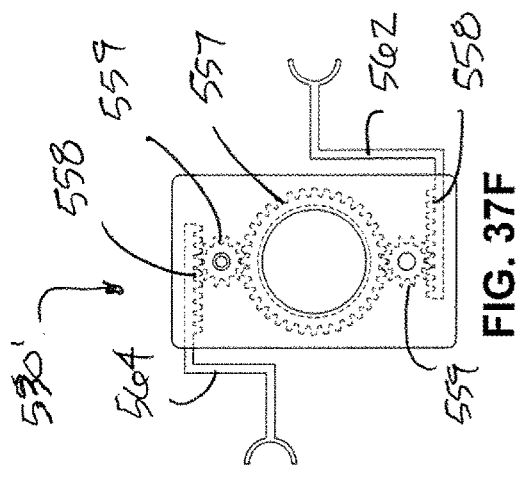
Figure 37F:
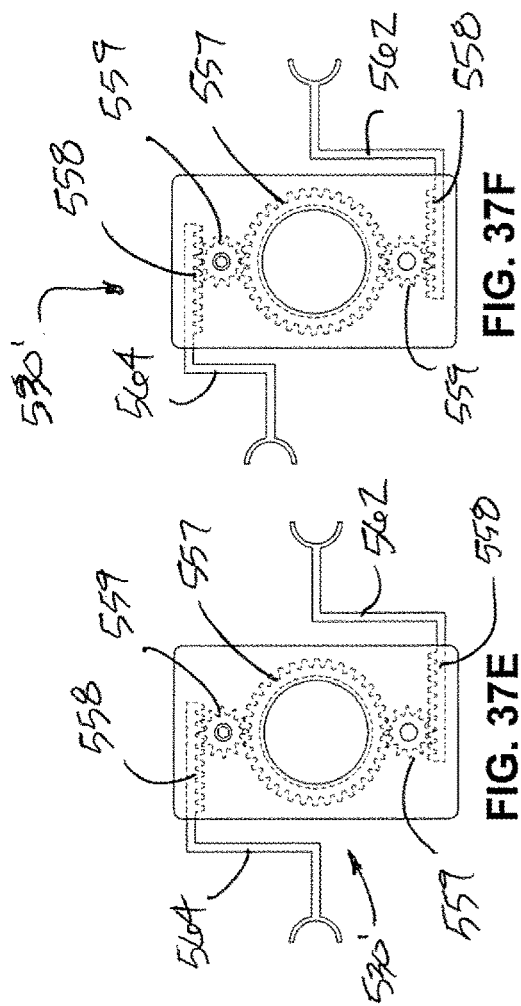

FIG. 30A is a front perspective view of a surgical device according to yet another embodiment of the present disclosure;

FIG. 30B is a front perspective view of the access port of the surgical device of FIG. 29A;

FIG. 31A is a side perspective view of the surgical device of FIG. 29A;

FIG. 31B is a side elevation view of the surgical device of FIG. 30A;

FIG. 31C is a rear elevation view of the surgical device of FIG. 29A in a first position of use;

FIG. 31D is a rear elevation view of the surgical device of FIG. 29A in a second position of use;

FIG. 32A is a side elevation view of the access port of FIG. 29B in a first position of use;

FIG. 32B is a side elevation view of the access port of FIG. 29B in a second position of use;

FIG. 33A is a detailed perspective view of the surgical device of FIG. 29A;

FIG. 33B is another detailed perspective view of the surgical device of FIG. 29B;

FIG. 34 is a view of various components described in relation to FIGS. 29A through 33B in an unassembled state;

FIG. 35A is a side perspective view of a surgical device according to yet another embodiment of the present disclosure;

FIG. 35B is a rear elevation view of the surgical device of FIG. 35A;

FIG. 36A is a side perspective view of the surgical device of FIG. 35A;

FIG. 36B is another side perspective view of the surgical device of FIG. 35A;

FIG. 36C is a detailed view of the surgical device of FIG. 36B;

FIG. 37A shows the surgical device and adjustment mechanism of FIG. 35A in a detailed view;

FIG. 37B shows the surgical device and adjustment mechanism of FIG. 37A in a second position;

FIG. 37C shows the surgical device and adjustment mechanism of FIG. 37A in a third position;

FIG. 37D shows the adjustment mechanism of FIG. 37A with the barrel removed;

FIG. 37E shows the adjustment mechanism of FIG. 37D in a second position;

FIG. 37F shows the adjustment mechanism in a third position; and

Figure 38:
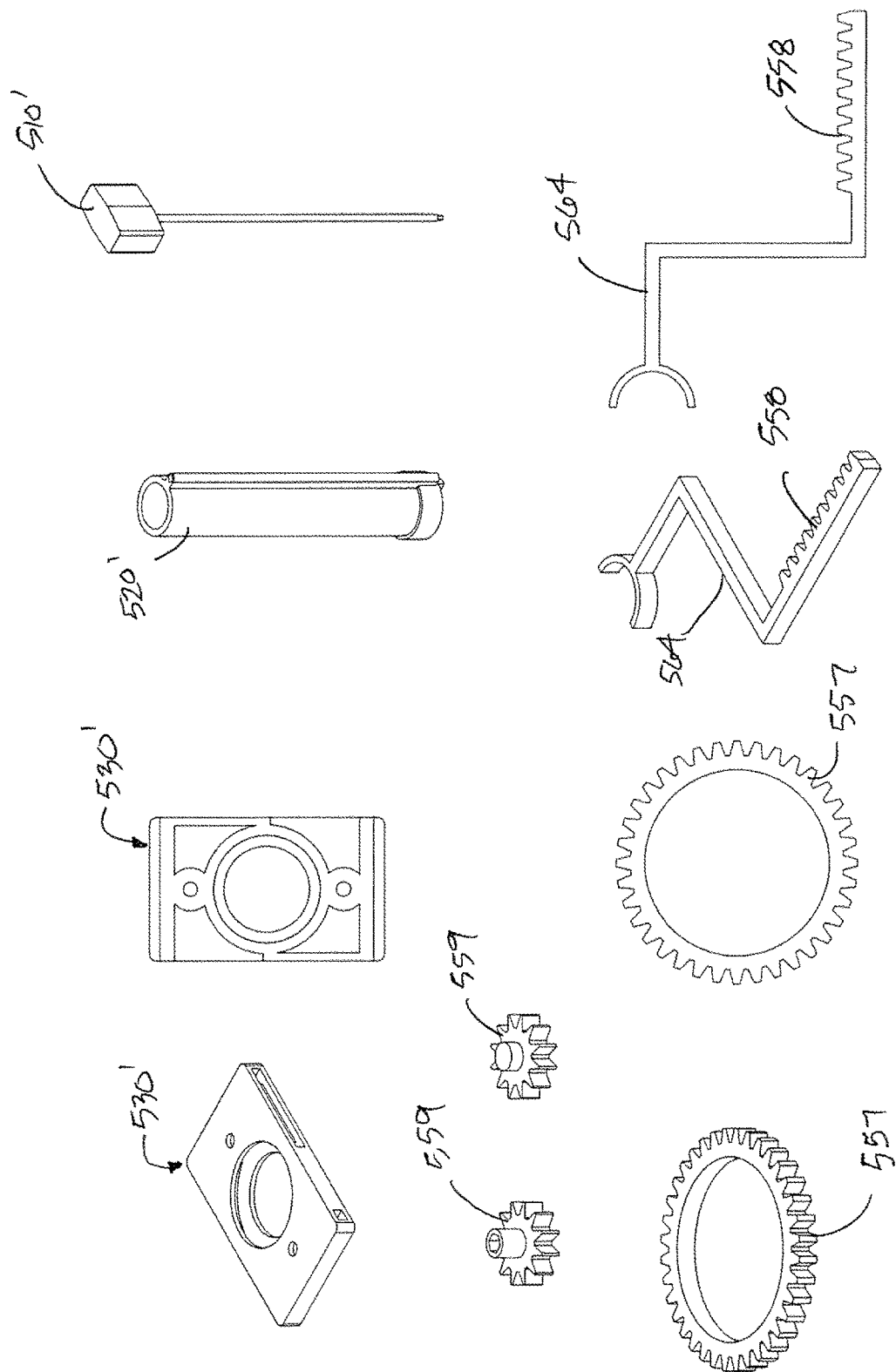

FIG. 38 is a view of various components described in relation to FIGS. 35A through 37F in an unassembled state.

DETAILED DESCRIPTION

Referring initially to FIG. 1, a surgical device 10 is illustrated for distraction of adjacent vertebrae and implantation of artificial intervertebral implants. The surgical device 10 may be described as both a distractor and as an implantor; for convenience herein, the surgical device 10 is referred to as an IDD 10. In use, a leading or operative end 12 of the IDD 10 is initially inserted between adjacent vertebrae in a first orientation, the IDD 10 then being rotated to a second orientation to fully distract the vertebrae for receiving an implant therebetween. One or more implants are loaded into a central cannula 14 of the IDD 10 and then forced advanced through the cannula 14, out from the operative end 12, and into the intervertebral space.

In greater detail, a form of the IDD 10 includes an elongated insertion and distraction portion referred to herein as a barrel 20 having the operative end 12 distally located from a stock end 22. The barrel 20 includes a loading chamber 24 which includes an opening 26 extending from the cannula 14 through the barrel 20 to the environment so that one or more implants may be inserted through the opening 26 and into the cannula 14.

The cannula 14 extends the entire length of the barrel 20. At the stock end 22, a rod 30 is disposed. The rod 30 may, in one use, be viewed as a push rod; however, a distal end 30a of the rod 30 may be connected with a dummy or trial device, such as a sizer, so that the trial device is inserted into the intervertebral space to determine a proper size for a subsequently-inserted implant, in which case the rod 30 would also pull in order to remove the trial device. The rod 30 may also consist of a plurality of rods (not shown), some or all of which may penetrate the implant or implants, partially or completely. These rods may move independently of one another, and to varying degrees, and may contact one or all components of a multi-component implant or a plurality of implants. Thus, the rod 30 (or rods) may also serve as a guide mechanism for the implant(s) thru the cannula 14, and beyond the barrel 20, and into the intervertebral space, to a predetermined location, for predicable deployment, as well as enable assembly of the of the implant(s) and components into a final construct in the intervertebral space. The loading chamber 24 allows access to the rod distal end 30a when the rod is in an at least partially retracted or withdrawn position. As an example, the rod distal end 30a may be threaded so as to be received within internal threads of an implant.

In another form, the rod 30 may be removed to allow a second rod or plunger (not shown) to be used for, as an example, a sizer or a targeting device. The targeting device may have a geometry matching or closely approximating that of the implants to be used. Use of the targeting device allows the user to manually and tactilely determine the shape (including contours) of the intervertebral size, as well as assess and select alignment of the IDD 10 with the vertebrae and intervertebral space. The second rod may provide a depth gauge, such as graduated or other depth markings, enabling a surgeon to determine the depth at which the implant should be inserted. In the subsequent implant insertion, the surgeon can operate the rod 30 to the same depth, or at least one determined based upon the use of the targeting device. Towards that end, the rod 30 may have graduated markings identical, similar, or corresponding to those of the second rod.

Accordingly, the rod 30 reciprocates to and between advanced and retracted/withdrawn positions within the cannula 14. The rod 30 may be withdrawn to be clear of the loading chamber 24, thus permitting an implant to be deposited into the loading chamber 24. The rod 30 may then be advanced or extended to a position so that the implant is forced beyond the barrel operative end 12 and, thus, inserted into the intervertebral space.

A distal section 40 of the barrel 20, including the operative end 12, is used for distraction of the adjacent vertebrae. A terminal portion 42 of the operative end 12 of the barrel distal section 40 has a reduced dimension to allow a portion thereof to be received between the adjacent vertebrae. More specifically, the operative end 12 includes a major dimension 44 extending in a first direction and a minor dimension 46 extending in a second direction. During initial insertion of the IDD 10 and, specifically, of the terminal portion 42 between the vertebrae, the major dimension 44 is aligned laterally and generally parallel to the general plane of the natural disc and intervertebral space (which is generally horizontal in an erect human, transverse to the longitudinal extent of the spine).

After initial insertion of the terminal portion 42, the user then proceeds to force vertebral distraction. The user may apply an axial force along the longitudinal direction, thus utilizing a wedge or chamfer 42a formed on the terminal portion 42 to provide an initial distraction amount.

Regardless, the user rotates the terminal portion 42 to cause distraction of the adjacent vertebrae. Generally speaking, the entire IDD 10 is rotated so that the major dimension 44 of the operative end 12 is shifted from the first orientation generally aligned with the small intervertebral space to a second orientation to be aligned with the superior-inferior longitudinal spinal axis (rostral-caudal). This movement necessarily forces the adjacent vertebrae apart, the outer surface 42b (such as radiused corners, FIG. 2) of the terminal portion 42 acting as a cam surface. In the preferred form, minor sides 50 of the terminal portion 42 are shaped so that the compression exerted on the minor sides 50 by the adjacent vertebrae maintains the terminal portion 42 in position in the second orientation and, more broadly, so that the entire IDD 10 is maintained with the major dimension 44 aligned with the longitudinal direction of the spine.

It is also preferred that the terminal portion 42 includes stops 60 formed on the terminal portion 42. In a first form, the stops 60 are formed as shoulders 62 on major sides 52 to limit the amount of insertion of the IDD 10 between the vertebrae. The stops 60 provide a predetermined position relative to at least sides of the vertebrae and, more preferably, a predetermined position relative to the invertebral space. More specifically, with a knowledge of the intervertebral dimensions and contours, and a knowledge of the size and shape of the vertebrae, the IDD 10 can be placed at a specific and known location relative to those features via use of the stops 60. As such, a user is able to insert an implant in a specific spot within the intervertebral space. In a further form, stops 60 may also be formed as shoulders 64 on the minor sides 50. The stops 60 may be formed on a selectively positionable member (not shown) so that a user may adjust the position of the stops relative to the ultimate tip of the terminal portion, or position the angle of the stops 60 relative to the longitudinal axis of the cannula 14 allowing the stops 60 to accommodate the vertebral aspect shape.

The distal section 40 of the barrel 20 includes longitudinal slots 70. The slots 70 allow the distal section 40 to be compressed during initial insertion.

After rotation of the terminal portion 42, the IDD 10 may be operated to advance an implant through the cannula 14 and into the intervertebral space. It should be noted that, should a user desire, the cannula 14 may be used to perform all modes of disc space preparation, such as a discectomy or nucleotomy or for a trial or sizing device, for instance, and as a minimally invasive surgical technique.

The cannula 14 may have a uniform shape or non-uniform shape in both the longitudinal direction and in cross-section. For instance, the rod 30 may be closely fit through a proximal section 14a of the cannula 14, thus serving as a guide to control the reciprocation of the rod 30. A cannula distal section 14b may have a different size or cross-sectional shape from that of the proximal section 14a so that the rod 30 passes easily therethrough.

In the preferred form, the distal section 14b has a cross-sectional shape corresponding to the shape of an implant. This cross-sectional surface shape may include additional features or projections, such as ribs or rails, that further guide or orient the implant into a predetermined position. As can be seen in FIG. 2, one form of the cannula 14 has a rectangular cross-sectional shape for use with an implant of similar or identical cross-sectional shape.

Notably, the cross-sectional shape of the distal section 14b corresponds to, but need not be identical to, the cross-sectional shape of an implant. In use, once the terminal portion 42 has been rotated to distract the vertebrae, the cannula distal section 14b may taper inwardly, prior to the implant being advanced through the cannula distal section 14b by the rod 30. In this position, the terminal portion 42 generally remains in the somewhat compressed state due to the insertion and distraction process, both in the direction of the minor dimension 44 as friction and pressure between the terminal portion 42 and the vertebral endplates does not generally permit normal, elastic return to a natural position, and in the direction of the major dimension as the vertebrae exert a compressive force on the minor sides 50.

The distal section 14b is expanded by the advancing implant. As the implant is forced through the distal section 14b by the rod 30, the major sides 52 are forced laterally outwardly. In some forms, the minor sides 50 are also forced outwardly (superior-inferior direction, rostral-caudal direction) to provide additional distraction. Again, expansion and contraction of the distal section 14b is permitted by the slots 70.

As described, the distal section 14b acts somewhat as a guide rail. Discussed above, the stops 60 provide a user with a known or ascertainable starting position, relative to the vertebrae. The close-fit and co-operation of the distal section 14b with the implant shape allow a user to have a definite knowledge of where and in what orientation the implant exits the cannula 14. Again, the use of the above-described targeting device/sizer and/or graduated markings on the rod 30 also help the user locate the implant at a known position.

After the initial implant or implant component has exited from the distal section 14b and into intervertebral space, a multitude of subsequent components may be delivered into the intervertebral space in a similar fashion, trailing the initial component, and forcibly driven together into a final assembly by the rod 30 or rods. Throughout this sequential process, the distal section 14b is ready for further implants or implant material. The distal section 14b likely compresses somewhat in the rostral-caudal direction (shortening the major dimension 44 by compressing the slots 70 thereof). The distal section 14b may or may not compress in the lateral direction (e.g., for shortening the minor dimension 46) due to residual force thereon from the endplates. The rod 30 or rods may be retracted or withdrawn so that its leading end is clear of the loading chamber 24 and received in the cannula proximal section 14a. A subsequent implant or implant material may then be loaded into the loading chamber 24 for advancement into the intervertebral space via a second advancement of the rod 30. Such allows additional implantation without requiring removal or re-insertion of the IDD 10, as described for prior art in the background. Furthermore, the placement of multiple implant components in the chamber, placed one behind the other, or placed side-by-side, allows the rod 30 or rods to deliver implants to the intervertebral space in a simultaneous and or sequential fashion. For instance, implants that are constructed of simultaneously or sequentially inserted components are advantageously accommodated by the IDD 10, as well as fusion procedures in which graft material may be subsequently packed into the intervertebral space and/or into cavities formed in and around the implant itself.

The IDD 10 is designed to protect, or avoid, adjacent tissues including neural tissues. Prior to and during initial insertion of the IDD 10, a sheath or skirt 77 is positioned around the terminal portion 42. The skirt 77 prevents or limits the ability for tissues to be caught by the slots 70 or the stops 60. In various exemplary forms, the skirt 77 may then be refracted to expose the slots 70 and stops 60, and/or the skirt 77 may be positioned to extend rearwardly from the stops 60 simply expand to accommodate the expansion of the slots 70 when an implant is advanced through the distal section 14b of the cannula 14.

As illustrated, the IDD 10 is operated in a pistol-trigger fashion, though a rotating knob (not shown) or other actuator type may be employed. As can be seen in FIG. 1, the barrel 20 is supported by and secured with a grip 80. The grip 80 allows the user to manipulate the IDD 10 generally with a single hand. A trigger 82 is hinged with the grip 80 and is spring-biased so that an actuator end 82a angles downwardly and away from the grip 80. When the trigger 82 is actuated by a user, the actuator end 82a is pulled (such as by fingers of the single hand) towards the grip 80, an upper, rod end 82b of the trigger 82 moving forwardly toward the operative end 12 of the IDD 10. The rod end 82b contacts or mates with the rod 30 to incrementally advance the rod 30 and an implant in the cannula distal section 14b or loading chamber 24.

Initial advancement of the rod 30 may be manually, such as by simply forcing the rod 30 forward by applying force to the end thereof protruding from the barrel 20. Once force is required, the trigger 82 may be employed. The engagement between the trigger rod end 82b and the rod 30 is such to permit slipping therebetween when the rod 30 is being advanced forward relative to the trigger 82. In one form, the trigger rod end 82b and the rod 30 may frictionally engage, while in another form the rod 30 may have a series of notches (not shown) that act in a ratchet manner with the trigger rod end 82b, though other mechanisms may be employed.

In a preferred form, the IDD 10 is easily cleaned and sterilized. To facilitate removal of particulate matter, the IDD 10 may be disassembled by removing a pivot pin 84 for the trigger 82 and removing the barrel 20 from the grip 80, the rod 30 also be removable through the cannula proximal section 14a and the skirt 77 being removable from either end of the barrel 20.

The implants may be any type of partial or total disc replacement implant, and may be any type of implant such as natural or artificial bone graft material, fusion boxes or cages, expandable devices, sequentially-constructed devices, hydrogel- or hydrophilic-based devices, or others made of metallic, polymeric, elastomeric, ceramic, materials, or combinations of these types.

In one form, the IDD 10 may be secured with a spinal fixation system such as a pedicle screw installed on a vertebrae prior to use of the IDD 10. This promotes maintaining the IDD 10 in the selected and desired position determined by the user during use of the trial or targeting devices, discussed above, for instance.

It should be noted that the operative end 12 and terminal portion 42 may have a variety of exterior or surface configurations. The terminal portion 42 has been illustrated and impliedly discussed as being generally rectangular, as shown for FIG. 1. Beyond this, the preferred form has, at minimum, radiused corners 53 to facilitate rotation of the terminal portion 42 between and against the vertebrae. In various forms, the corners 53 need not be identical, such as by providing a single direction of rotation for the terminal portion 42. Moreover, the major and minor dimensions 44, 46, and their respective sides, may also be viewed as corresponding to a racetrack-shape having curved or circular minor sides connected by straight sides, or may be viewed as an oval or elliptical having major and minor axes, as mere examples. As illustrated in FIGS. 3 and 4, an alternate form of a barrel 20' may have a circular or cylindrical outer surface 21', with a rectangular cross-section for cannula distal section 14b' that varies from a larger size (FIG. 3) proximal the loading chamber 24 to a smaller size (FIG. 4) closer to or at the terminal portion 42.

A second form of an inserter/distractor device or IDD 100 is illustrated in FIGS. 6, 6A, and 6B. In simple terms, the IDD 100 has a small dimensioned profile or leading portion 110 for initial insertion between adjacent vertebrae. Unlike the above-discussed IDD 10, however, the IDD 100 is not rotated, instead operating to expand and distract the vertebrae by relative shifting of two components.

In the illustrated form, the IDD 100 includes an outer member 120 somewhat in the form of a sleeve having a cannula 122. The outer member 120 may include stops 60 for providing a predetermined or known position relative to the vertebrae. A leading end 124 is positioned between the vertebrae, up to the stops 60. After the initial insertion of the leading end, an inner member 130 is moved relative to the outer member 120 to expand the outer member 120. More specifically, the outer member 120 is illustrated as having a somewhat quadrilateral shape, similar to that of IDD 10, with rostral-caudal sides 126 corresponding to a lateral dimension (into the plane of FIG. 6) and having lateral sides 128 corresponding to a rostral-caudal dimension 129. When expanded, the distance between the rostral-caudal sides 126 (across the cannula 122) are increased, increasing the rostral-caudal dimension 129. At least each of the lateral sides 128 includes a longitudinally extending slot 121 that permits such expansion. In other forms, a plurality of slots (not shown) may be provided on the outer member 120, such as slots (not shown) on the rostral-caudal sides 126 and additional slots (not shown) on the lateral sides, each of these other slots allowing for additional expansion due to an implant passing therethrough, as is described above for the IDD 10, and a skirt 77 (FIG. 5) may also be provided.

In the illustrated form, the inner member 130 is a partial sleeve, having a sleeve-like body portion 132 closely received within the outer sleeve cannula 122 and having forwardly or distally extending arms 134. The arms 134 each have a small wedge 136 facing outward and engaged in respective minor side slots 121, which themselves may have angled surfaces 121a as shown in FIG. 6. As the inner member 130 is retracted, the wedges 136 are forced rearwardly through the slots 121, thus expanding the slots 121 and the minor sides 128 so that the major sides 126 are moved apart to distract the vertebrae.

There are a number of variations on the IDD 100. For instance, the shapes of the wedge 136 and slot 121 could be reversed so that advancing the inner member 130 (as opposed retracting, as discussed) forces the slots 121 to widen. The inner member 130 may be simply the pair of arms 134, without the body portion 132, or the body portion may be some other type of bridge allowing the arms 134 to be manipulated jointly. In another form, the inner member 130 may be entirely sleeve-like through the portion of the IDD 100 that the implant would pass, but for the wedges 136 protruding therefrom. In another form, the rod 30 may be connected to the inner member 130 so that, either prior to or in combination with the implant reaching the distal-most portion of the IDD 100, movement of the rod 30 causes the wedges 136 to shift and widen the slots 121 to expand the IDD 100.

These forms of the IDD 100 have distinct benefits over the prior art. For instance, the construction of the IDD 100 minimizes the amount of distraction that is necessary for an implant to pass therethrough. As the wedges 136 are to the lateral sides 128 (in the lateral direction), the amount of rostral-caudal distraction need not accommodate the wedges 136 nor, in a number of described forms, the inner member 130. This is in contrast to the design of the '875 application discussed in the background where a significant amount of distraction is required simply to allow the distractor components to remain between the vertebrae as the implant passes therethrough. Movement of the wedges 136 can also be calibrated so that a particular amount of retraction of the inner member 130 corresponds to a known amount of distraction.

In some forms, the slots 121 and wedges 136 may cooperate to form stops 150 for maintaining the wedges 136 in a desired position. FIG. 7 illustrates a stop 150 in the form of small barbs 152 that the wedge 136 passes beyond when being retracted. The wedge 136 is thus unlikely to inadvertently slip or return over the barbs 152 during use of the IDD 100, that is, without a user intentionally forcing the wedge 136 over the barbs 152.

FIG. 8 illustrates a stop 150 in another form, specifically flats 154 formed on the surfaces of the slot 121 and flats 156 formed on the wedges 136. When the wedges 136 reach the slot flats 154, the pressure on the wedges 136 that would tend to expel the wedges 136 therefrom is reduced or even eliminated, with simply a compressive force on the wedges 136. While the wedge flats 156 are not required, they assist with movement of the wedges 136 against the slot flats 154, as the wedges 136 may otherwise bite into or grind against the slots 121. Although not shown, edges of the wedges 136 may be rounded so that the inner member 130 and wedges 136 may be rotated relative to the slots 121 and outer member 120 in order to release the wedges 136 from the slots 121 and, more particularly, quickly release the stops 150.

It should also be noted that the slots 121 may have a varying contour for more controlled distraction. That is, as the distraction at the distal-most end of the IDD 100 is based on an angular opening of the slots 121, the geometry of the wedges 136 and slots 121 may be designed so that equal amounts of movement of the wedges 136 along the slots results in equal amounts of gross distraction for the IDD 100.

According to another embodiment of the present disclosure, a surgical device 200 is shown in FIGS. 9A and 9B. In certain embodiments, the surgical device 200 may be used to facilitate distraction of the laminar arch of a patient.

FIG. 9A shows the surgical device 200 in a side perspective view. According to this embodiment, the surgical device 200 includes a grip 280 and trigger 282 which are configured to manipulate ratcheting mechanism 270 and thereby position ratchet elements 273, 275 in an engaged or disengaged position against rod 230. In FIG. 9A, ratcheting elements 273, 275 are shown in the engaged position and are positioned against an outer surface of rod 230.

Rod 230 is preferably configured to be received within an opening 226 of barrel 220, as described in various embodiments herein. Barrel 220 may preferably comprised of two sections 220a and 220b. Barrel sections 220a and 220b may further comprise corresponding and partially overlapping surfaces to permit section 220a to be substantially congruent with 220b, or to permit separation of section 220a from 220b, as explained in further detail below.

Referring now to FIG. 9B, the surgical device 200 is shown in a front perspective view. An opening 226 extends substantially through barrel section 220a and 220b and may permit one or more implant materials to be inserted therethrough. According to this embodiment, operation of trigger 282 may be accomplished by a user as described above, whereby squeezing trigger 282 against grip 280 operates ratcheting mechanism 270 and advances rod 230 in a generally longitudinal direction relative to barrel 220.

According to one embodiment, the advancement of rod 230 in barrel 220 causes distraction of barrel. The use of ratcheting mechanism 270 permits the advancement of rod 230 to occur in a sequential and predetermined manner. In one embodiment, rod 230 may be tapered to achieve the desired level of distraction and the predetermined stages of advancement within barrel 220. In one embodiment, ratchet elements 273, 275 are operable by use of trigger 282 and serve in part to secure rod 230 in the proper location relative to barrel for each sequential stage of advancement. In another embodiment, the ratchet elements 273, 275 may be selectively engaged or released from the rod 230 at the user's preference.

According to yet another embodiment, the rod 230 may be substituted with multiple rods or dilators. In one embodiment, the dilators are tapered and cause distraction of barrel 220 as dilators are advanced into barrel 220 as described above in relation to FIG. 9B. In varying embodiments, the rod or dilators may be substantially circular in cross-section, or may be substantially oval-shaped, elliptical, rectangular, or other shapes including polygon.

Various stages of advancement of rod 230 relative to barrel 220 are shown in FIGS. 10A-10D. FIG. 10A shows the surgical device 200 in a first operative position with the rod 230 completely separated from barrel 220. The use of trigger 282 in conjunction with ratcheting mechanism 270 provides a user with an easy to operate mechanical device, which does not require excessive force and provides distraction that is predictable and repeatable.

FIG. 10C shows another operative position, wherein rod 230 has been advanced within barrel 220. FIG. 10D shows the surgical device 200 in an intermediate position wherein rod 230 is partially advanced within barrel 220 and further comprises one or more serial dilation rods, as described briefly above and in the following paragraphs.

According to one embodiment, the surgical device may further include one or more serial dilation rods, such as those shown in FIG. 11A. According to this embodiment, the surgical device 200 may advance a first dilating rod, followed by a second dilating rod, followed by a third dilating rod, which are depicted in FIG. 11A as 292, 294 and 296. According to yet other embodiments, fewer or greater number of dilating rods may be employed than shown in FIG. 11A.

Referring now to FIG. 11B, the surgical device according to FIGS. 9A and 9B is shown in a side elevation view with the serial dilators 292, 294, 296 inserted within barrel 220. FIG. 11C shows a front elevation view of the surgical device according to the embodiment of FIG. 11B. In operation, embodiments of the surgical device shown in FIGS. 11A-11C permit the user to advance various rods or dilators serially to permit progressive distraction of barrel sections 220a and 220b. Once the desired level of distraction of barrel sections 220a and 220b has been accomplished, the user may further insert a final stage rod or dilator, which according to one embodiment may be employed to establish an access portal to the intervertebral space, by way of example. In this embodiment, a final stage rod or dilator may also permit the serial dilators 292, 294, 296 to be removed from barrel 220. In certain embodiments, the level of distraction is not dependent on the diameter of the final serial dilator. In certain embodiments, the user may also observe the level of advancement of the dilators within the surgical device to maintain depth control.

Referring now to FIG. 12, one embodiment of the surgical device is shown, which comprises a selectively removable access portal 310. Access portal 310 may be used with the surgical device 200 described above or according to any of the embodiments described herein. According to this embodiment, once the series of dilators have been inserted into the barrel 220 of the surgical device 200 to achieve the desired distraction, and the first and second serial dilators are removed, the access portal 310 may be inserted through the largest of the serial dilators 296. In other embodiments, the access portal may be inserted prior to the final serial dilator is removed.

According to one embodiment, the access portal 310 comprises a distal end 312 to maintain the desired distraction between, for example, an intervertebral space, and further comprises an operative end 311 for manipulation of the access portal 310. Referring now to FIGS. 13A and 13B, a top elevation view and a front perspective view of the access portal 310 are shown, respectively. Referring in detail to FIG. 13A, the access portal 310 is shown in both a first or closed position (upper drawing) and a second or opened position (lower drawing). In the closed position, access portal 310 is shown with the operative end 311 in a first position, which causes a corresponding slider 313 to be positioned near or adjacent the distal end 312. In the second or opened position, the access portal 310 has the operative end 311 in a second position and a corresponding position of the slider 313 removed from the distal end 312, as shown in FIG. 13A.

According to one particular embodiment, the slider 313 may include a plurality of apertures, which permit the legs 315 of access portal 310 to slide therethrough. Accordingly, as a user pushes or pulls operative end 311 of access portal 310, the legs 315 are opened or closed relative to the position of slider 313 about the longitudinal axis of legs 315. In yet another embodiment, the access portal 310 may comprise a collar or ring to maintain distraction although access portal 310 may be removed or adjusted, for example, to achieve a different degree of distraction. In yet another embodiment, the access portal may be actuated by an existing power supply as opposed to manually actuated. Further illustration is shown in connection with FIG. 13B and the components depicted in FIG. 14.

Referring in detail to FIG. 13B, the access portal 310 is shown in a front perspective view. The distal end 312 may be formed of any shape, size, or orientation, including but not limited to that shown in FIG. 13B. According to one embodiment, the distal end 312 may include one or more components which are selectively removable from the body of the access portal 310. According to one embodiment, the operative end 311 may be pushed or pulled to operate the slider 313 relative to the legs 315, and may further be rotated to permit removal of the distal end 312 from the body of the access portal 310. A complete set of components of the access portal 310 may be seen in FIG. 14 in a disassembled state.

Referring now to FIGS. 15-19, another embodiment of the present disclosure is shown. According to this embodiment, a surgical device comprises a cam mechanism 350 located on the distal end of surgical device 300, which permits both distraction and delivery of one or more implant materials through the barrel 320 of the surgical device 300.

Referring in detail to FIG. 15, a front perspective view of the surgical device 300 is shown. According to this embodiment, the cam mechanism 350 is interconnected to a trigger 382, which is further coupled to grip 380, and which are mechanically linked to achieve rotation of cam mechanism 350, as described in greater detail below. A mechanical linkage 390 preferably interconnects first cam section 392a and second cam section 392b to slider 375, which is further connected to trigger 382 (not shown in FIG. 15). Referring to FIGS. 16A and 16B, a side elevation view and detailed view of the surgical device 300 are shown, wherein the device is in a first position. In this position, a user may insert the distal end of the surgical device 320 into the operative site of a patient. The user may thereby position the cam mechanism 350, for example, between two vertebrae.

As shown in the detailed view of FIG. 16B, when the surgical device is in a first position, the first and second cam sections 392a, 392b are substantially aligned. The linkage 390 between trigger 382 and cam mechanism 350 is also shown in a first position.

Referring to FIGS. 16C and 16D, the surgical device 300 is shown in a second position. Referring in detail the detailed view FIG. 16D, the first cam section 392a has been rotated downwardly or in a generally clockwise direction, and second cam section 392b has been rotated upwardly or in a generally counterclockwise direction. This rotation is caused by the trigger 382 being squeezed relative to grip 380, as shown in FIG. 16C. Depressing trigger 382 causes slider 375 to move longitudinally, which in turn causes a corresponding movement to linkage 390 in a general longitudinal direction. Movement of linkage 390 in turn causes pins 394 to move within slots 395, as best shown by comparing FIGS. 16B and 16D. This rotation of pins 394 within slots 395 causes rotation as shown in FIG. 16D of first cam section 392a and second cam section 392b, which increases the distraction between the intervertebral space.

Referring back to FIG. 15, the rotation of first and second cam section 392a, 392b further causes aperture 326 to be positioned such that one or more implant materials may be passed through barrel 320 and exit aperture 326. Thus, aperture 326 is aligned with the longitudinal access of barrel 320 when first and second cam section 392a, 392b are in a second position, as shown in FIG. 16D. This step may be repeated for varying implant materials and corresponding varying levels of distraction.

Referring to FIGS. 17A and 17B, the surgical device 300 is shown in a top plan view. FIG. 17A shows the surgical device 300 in a first position, corresponding to the position shown in FIG. 16A. FIG. 17B shows the surgical device 300 in a second position, corresponding to FIG. 16C. As with previously described surgical devices, surgical device 300 permits incremental distraction, and may further permit both distraction and expansion. In one embodiment, this is achieved by providing cooperating cam elements, which rotate to distract, and may also expand outwardly once distracted to expand the distal end of the surgical device 300 in a lateral direction. In this manner, one or more implant materials of a larger size may be delivered through the distal end of surgical device 300, as will be understood from the following description.

FIG. 17C shows the surgical device 300 in another front elevation view. FIG. 17D is a detailed view of the front elevation view of surgical device 300, demonstrating how apertures 326 of first and second cam sections 392a and 392b are aligned with barrel 320, and thereby permit one or more implant materials to be delivered therethrough. FIG. 17D also demonstrates how first cam section 392a and second cam section 392b may be rotated to achieve greater distraction than when cam mechanism 350 is in a first position, as shown in FIG. 16A.

FIG. 18A shows a side perspective view of the surgical device of FIG. 15, including an implant material and implant material insertion instrument. FIG. 18B is another side elevation view of the surgical device of FIG. 18A shown in a second position. According to certain embodiments, the operation of trigger 382 may actuate both rotation and/or expansion of cam sections 392a and 392b, but may also advance rod 399 within barrel 320. The rod 320 preferably comprises an operative end 397 and a distal end 396, the distal end 396 capable of receiving one of several types of implants, including implant I as shown in FIG. 18A. In one embodiment, the actuation may cause the rod 399 to advance longitudinally within barrel 320, and may cause rotation of rod 399 to rotate an implant I through the surgical device 300 and in a desired orientation prior to delivery through the distal end of surgical device 300. In certain embodiments, the advancement and/or rotation of rod 399 may be achieved by a secondary trigger (not shown in FIGS. 18A-B).

Rod 399 may further comprise one or more indicia (not shown) to allow a user to visually determine the depth or advancement of rod 399 within barrel 320. In other embodiments, the rod 399 may further comprise ribs, threading, or other surface irregularities that provide a hard stop, preventing advancement of rod 399 beyond a desired location. In yet other embodiments, the surface irregularities may further facilitate rotation of rod 399 within barrel 320, such as by providing a threaded surface of rod 399 corresponding to a threaded interior surface of barrel 320.

FIGS. 18C-D include side perspective views of the surgical device according to another embodiment of the present disclosure. The surgical device shown in FIGS. 18C-D comprises a plurality of notches 398 along the length of rod 399, which preferably assist in ratcheting of the rod 399 through the longitudinal axis of barrel 320. According to a preferred embodiment, the ratcheting insertion of rod 399 may be accomplished by use of a second trigger 382b, which incrementally advances the rod 399 and thereby advances the position of an implant I. FIGS. 18E-F are detailed top perspective views of the surgical device according to another embodiment of the present disclosure. In this particular embodiment, the plurality of notches 398b are located along an outer top surface of the frame of the surgical device, and facilitate selective placement of a stop 396. The stop 396 may be placed at the preference of the user to prevent the distal end 397 from advancing past the stop 396, as best shown in FIG. 18F.

FIGS. 18G-J depict various views of a surgical device according to yet another embodiment of the present disclosure. In this embodiment, a modified rod is provided comprising a first portion 399b and a second portion 399c, which are configured to move relative to each other in at least one plane. The surgical device of this embodiment includes a plurality of notches 398c along at least one surface of the barrel of the surgical device, as shown in FIG. 18H. The plurality of notches 398c allow a post 387 to be received within any one of the notches and at a desired location along the longitudinal length of the barrel. The post is coupled to a movable arm 388, which may be oriented by rotating the post 387 within any one of the notches 398c, as best shown in FIG. 18H. Referring now to FIGS. 18I-J, the arm 388 may be positioned to redirect second rod portion 399c after implant I has advanced through the distal end of the barrel as shown in FIG. 18I. In one embodiment, the user may rotate the post 387 either before or after the rod portions 399b, 399c have been advanced through the barrel of the surgical device. According to at least one embodiment, the implant I may be connected to the distal end of second rod portion 399c such that the implant I is free to pivot prior to being released from the second rod section 399c, as shown in FIG. 18J.

FIGS. 18K-N are perspective views of an insertion rod for use with the surgical devices according to one embodiment of the present disclosure. The rod 399 according to this embodiment comprises at least one internal lumen, which may house one or more tines P1, P2 for coupling the rod 399 to an implant I, such as the one shown in FIG. 18N. The rod 399 of this embodiment may comprise a tip T which separates two tines P1, P2 as they are advanced longitudinally from the rod 399 inner lumen. In one embodiment, the tines are advanced by advancing the operative end 397 of rod 399 within the inner lumen of the rod 399. In another embodiment, the tines P1, P2 may be manipulated by rotation of operative end 397 relative to rod 399. Tines P1, P2 preferably comprise means for latching, hooking, grasping or otherwise selectively attaching to implant I.

In one embodiment, surgical device 300 may be comprised of a material that permits impaction on the operative end of the device, for example with a mallet. In another embodiment, the rod 399 has an operative end 397 that is configured to receive an instrument to achieve delivery of a corresponding implant I, such as but not limited to a mallet.

Various views of components for the surgical device 300 according to this embodiment are shown in an unassembled state in FIG. 19.

Referring now to FIGS. 20-24, another embodiment according to the present disclosure is shown. Referring in detail to FIG. 20A, a side perspective view of a surgical device 400 is shown relative to adjacent vertebral bodies. Referring to FIG. 20B, a front perspective view of the surgical device 400 is shown. The surgical device 400 according to this embodiment comprises a barrel 410 with an aperture 426 therethrough, which facilitates insertion of one or more implant materials. The surgical device 400 also includes a ratcheting mechanism 420, which permits a level of mobility and/or distraction of the ratcheting mechanism at the operable end of the surgical device 400.

As explained in more detail below, the surgical device 400 comprises at least one gear 430 and a plurality of arms 442, 444 which are positioned on opposing sides of the barrel 410, and which may be selectively positioned against or attached to one or more screws 412, 413 inserted into, for example, adjacent vertebral bodies.

The surgical device 400 preferably provides independent distraction on each lateral side of the barrel 410. The positioning and manipulation of arms 442, 444 also permits a user to adjust the location of the port laterally relative to the intervertebral space shown in FIGS. 20A-B. As described in greater detail below, the barrel also permits a quick connection or disconnection from the ratcheting mechanism 420, if desired.

Detailed views of the surgical device 400 are shown in FIGS. 21A-D. Referring now to FIG. 21A, a side perspective view of the surgical device 400 is shown. Attention is drawn to the detailed section of surgical device 400, which is enlarged and depicted in FIG. 21B. Referring to FIG. 21B, the ratcheting mechanism 420 further comprises, according to a preferred embodiment, at least one gear 430, which interfaces with at least one linear gear element 431, which permit corresponding leg 442 and coupling mechanism 443 to move laterally with respect to ratcheting mechanism 420 during operation of the surgical device 400. The ratcheting mechanism 420 permits varying height and location of the surgical device 400 relative to the surgical site, as may be seen from comparison of FIGS. 22B and C.

Referring to FIG. 22A, a complete assembly of the ratcheting mechanism 420 is shown in a front perspective view. According to this embodiment, the ratcheting mechanism 420 is comprised of a first adjustable element 423a and second adjustable element 423b, which are in communication with the barrel 410 of surgical device 400. In this manner, adjustable element 423a and adjustable element 423b may be manipulated by placing an item, such as cannula, dilator, instrument, tool or other item into the aperture 426 of the barrel 410 and thereby expand the aperture 426. This placement in turn forces adjustable element 423a and 423b laterally apart, as will be best understood by viewing FIGS. 23A and 23B. FIGS. 22B and C show the ratcheting mechanism 420 is a retracted and distracted position, respectively.

Referring to FIG. 23A, the ratcheting mechanism 420 is shown in a first position. The ratcheting mechanism 420 may further comprise one or more lock bars 432, which may be positioned to maintain the position of first adjustable element 423a and second adjustable element 423b when expanded to the desired location.

Referring to FIG. 23B, the ratcheting mechanism 420 is shown in a second position, wherein the aperture 426 has been expanded. According to a preferred embodiment, the locking bar 432 may be a rotatable lock bar, and may be positioned between teeth of gear 430, as shown in FIG. 23B. A depiction of the components of the surgical device 400 and ratcheting mechanism 420 are shown in an unassembled state in FIG. 24.

Referring now to FIGS. 25-28, an alternate embodiment from the one described in relation to FIGS. 20-24 is shown. According to this embodiment, the surgical device 400' further comprises a grip 450, and may further comprise a trigger for operating surgical device 400'. According to this embodiment, ratcheting mechanism 420' may comprise a plurality of lock bars 432' as shown in FIG. 27A-27C. FIGS. 26A-C depict a surgical device similar to the surgical device 400 described above, except the arms are fixed relative to the ratcheting mechanism to permit greater stability.

Various detailed views of the ratcheting mechanism 420' according to one embodiment are shown in FIGS. 27A-C. Accordingly, in at least one embodiment, the lock bars 432' shown in FIG. 27A-27C may further operate as a ratcheting mechanism within the housing of surgical device 400', thereby maintaining the position of adjustable element 423a and adjustable element 423b relative to one another as they are expanded, as best shown in FIG. 27C. Release of the lock bars 432' may be accomplished by operating the trigger relative to the grip 450 of surgical device 400'. Various components of surgical device 400' are shown in an unassembled state in FIG. 28. It is expressly understood that these components are not necessarily to scale.

Referring to FIGS. 29A-B, perspective views of one particular surgical site are shown. In FIG. 29A, the boney anatomy is shown unaltered. In FIG. 29B, the laminar arch has been dissected to create a portal or window for use with the surgical device described in varying embodiments herein. The dissection of the laminar arch facilitates use of the surgical device to distract adjacent boney anatomical structures, as described and shown in relation to FIGS. 30-34.

According to another embodiment of the present disclosure, a surgical device 500 may comprises a barrel 520 and an adjustment shaft 510, which may be used to achieve distraction between two adjacent pedicle screws 511, 512. Referring now to FIGS. 30A and 30B, a front perspective view of the surgical device 500 and associated components are shown according to one embodiment.

Referring to FIG. 30A, surgical device 500 may be positioned between two adjacent vertebrae. The surgical device 500 preferably includes a longitudinal barrel 520, which has an extension for receiving an adjustment shaft 510, as shown in FIG. 30A. Surgical device 500 is modular and may be used in connection with a variety of differently configured access ports, as described in the following detailed description.

Referring to FIG. 30B, certain embodiments further comprise an access port 530, which may be positioned between adjacent vertebrae (noted by adjacent pedicle screws 511, 512 in each vertebrae). According to further embodiments, the access port 530 may further comprise a sleeve 540. The sleeve 540 may serve to protect from damage to surrounding neural elements or other anatomical features of the patient. In certain embodiments, the sleeve is made of an interwoven mesh, and is substantially deformable. In other embodiments, the sleeve 540 may be pre-formed prior to insertion between the adjacent vertebrae, as desired by the user, to protect from damage to surrounding anatomical features of the patient.

Referring now to FIGS. 31-32, the distraction capabilities of surgical device 500 are shown. Referring to FIG. 31A, the surgical device 500 further comprises an adjustment mechanism 512, which may be selectively engaged by adjustment shaft 510, as shown in FIG. 31A. According to this embodiment, rotation of adjustment shaft 510 causes rotation of adjustment mechanism 512, which in turn causes lateral movement of distraction plates 514, 516, as best shown in FIGS. 31C-31D.

Referring in detail to FIG. 31C, a rear elevation view of surgical device 500 is shown. In FIG. 31C, distraction plates 514, 516 are shown in a first position. Distraction plates 514, 516 are mechanically linked to adjustment mechanism 512 by one or more hinged members 517. Referring to FIG. 31D, surgical device 500 is shown in a back elevation view in a second position of use. According to this position, distraction plates 514, 516 have been adjusted laterally in relation to the position shown in FIG. 31C. This adjustment is achieved by rotating adjustment shaft 510 once engaged with adjustment mechanism 512, which in turn causes one or more hinged members 517 to distract distraction plates 514, 516 as shown in FIG. 31D. Accordingly, surgical device 500 is permitted to be adjusted laterally relative to the underlying surgical field, for example, an intervertebral space.

Although the embodiments described herein are shown within adjustment shaft that may be rotated by manual force, embodiments of the present disclosure are contemplated for use with various powered apparatus which are known to those of ordinary skill in the art. Such power sources would include, but are not limited to, pneumatic and/or electric power sources.

Referring to FIGS. 32A-32B, a side elevation view of the leave behind access port 530 and sleeve 540 are shown in corresponding first and second positions of use, as described above in connection with FIG. 31A and FIG. 31B, respectively. According to a preferred embodiment, access port 530 and sleeve 540 may be positioned prior to or following distraction of surgical device 500, and thereby permit access to the disc space between adjacent vertebrae, as shown in FIGS. 29A-29B.

The access port 530 and/or sleeve 540 may be rigid, semi-rigid, or deformable to a desired shape and contour. The materials may vary for each and include but are not limited to metals, metal alloys and polymeric materials. The access port 530 and/or sleeve 540 allow for vertical compression and adjustment relative to the underlying surgical field, and facilitate retraction of and avoidance of contact with soft and sensitive tissue surrounding the surgical field. In combination with the surgical device 500, these components are well suited for placing materials in an intervertebral disc space and/or at a patient's laminar arch. The access port 530 and sleeve 540 are adjustable to accommodate a variety of different surgical procedures and/or implant materials.

Referring now to FIGS. 33A-33B, the adjustment mechanism 512 and adjustment plates 514, 516 are shown in detailed views. Referring to FIG. 33B, the adjustment mechanism 512 may further comprise a lock bar 513, which engages adjustment mechanism 512 and maintains adjustment mechanism in the desired level of distraction. According to at least one embodiment, the adjustment mechanism may further comprise one or more securing members 515, which may be tightened and secured relative to adjustment mechanism 512 after distraction plates 514, 516 are in their desired position. Referring to FIG. 34, various components of surgical device 500 are shown in a disassembled state for further illustration of these components.

Referring now to FIGS. 35-38, an alternate embodiment of the surgical device described above in connection with FIGS. 29-34 is shown. According to this embodiment, surgical device 500' incorporates certain aspects described in relation to FIGS. 29-34 and also certain aspects of the embodiments described above in relation to FIGS. 22-28.

Referring to FIG. 35A, a side perspective view of surgical device 500' is shown. Surgical device 500' preferably includes an adjustment mechanism 530', which may be manipulated to cause adjustment of surgical device 500' by rotation of adjustment shaft 510', as described in greater detail below. Referring to FIG. 35B, a front elevation view of surgical device 500' is shown in a first position, and preferably located between two adjacent pedicle screws 511' and 512'.

Referring to FIGS. 36A-36C, the connection between adjustment shaft 510' and adjustment port 565 is shown in detail. Referring specifically to FIG. 36C, adjustment port 565 preferably comprises a hexagonal-shaped aperture, which may receive a hexagonal-shaped stem 560 located on distal end of adjustment shaft 510'. Other shapes of stem 560 and corresponding shapes of aperture of adjustment port 565 are contemplated for use with the present disclosure.

Referring now to FIGS. 37A-37C, the operation of adjustment mechanism 530' is depicted. According to the view shown in FIG. 37A, adjustment mechanism 530' may comprise two adjustment arms 562, 564, which may move laterally in relation to slot 561 of adjustment mechanism 530'. In addition, adjustment port 565 described above in relation to FIG. 36A may also move laterally relative to the underlying surgical field. Referring to FIG. 37B, the surgical device 500' and adjustment mechanism 530' are shown in a second position. Referring to FIG. 37C, adjustment mechanism 530' and arms 562, 564 are shown in a third position, whereby barrel 520' has been rotated to allow alignment of adjustment shaft 510' and adjustment port 565.

Referring to FIG. 37D, adjustment mechanism 530' is shown with the barrel 520' removed. As shown, the adjustment mechanism 530' comprises a connector 555, to which the barrel 520' may be quickly attached or detached by rotation of barrel 520' relative to connector 555. Various connection mechanisms are contemplated for use with the embodiments described above, including but not limited to a slide lock mechanism, a spring-loaded or biased detent, a movable lever, a snap-connection, a threaded connection, a friction or interference fit, a cam-locking surface, or a spring-loaded locking mechanism.

Referring to FIGS. 37E and 37F, the adjustment mechanism 530' is shown in a first and second position of use, respectively. According to the view shown in FIG. 37E, adjustment mechanism 530' may comprise a gear 559 which may be aligned substantially with adjustment port 565. Gear 559 is also preferably engaged by one or more teeth to second gear 557. Second gear 557 is preferably connected to another gear 559, which according to the embodiment shown in FIGS. 37E and 37F is substantially the same size and shape as gear 559. Gears 559 are preferably engaged by one or more teeth to threaded bars 558 which are mechanically linked or formed as one-piece with one of the respective arms 562, 564. In operation, rotation of adjustment shaft 510' (once engaged through adjustment port 565) causes rotation of gear 559, which in turn causes rotation of second gear 557 and gear 559, and lateral movement of bars 558.

Referring now to FIG. 37F, adjustment mechanism 530' is shown in a second position of use, whereby arms 562, 564 are moved laterally in relation to the body of adjustment mechanism 530'. Accordingly, adjustment of arms 562, 564, once engaged to pedicle screws 511', 512', may achieve distraction of the adjacent vertebrae as described above in detail in connection with FIGS. 22-28. Referring now to FIG. 38 components described above in relation to surgical device 500' are shown in an unassembled state to provide further illustration.

Although a specific form of adjustment and actuation is described above, it is expressly understood that other mechanisms may be incorporated without departing from the spirit of the present disclosure. For example, the distraction mechanism may be comprised or a worm gear, a rack and pinion assembly, a ratcheting assembly, a lever, a hydraulically-actuated assembly or by a electronically powered assembly.

While various embodiment of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims. For further illustration, the information and materials supplied with the provisional and non-provisional patent applications from which this application claims priority are expressly made a part of this disclosure and incorporated by reference herein in their entirety.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A surgical device for distraction and insertion of intevertebral implant material in an intervertebral space between adjacent vertebrae, the device comprising:
   an elongated barrel;
   an operative end formed on a distally-located end of the barrel, the operative end for engaging the adjacent vertebrae, wherein the operative end includes a plurality of slots allowing at least the operative end to be expanded, and includes a first dimension and a second dimension, wherein the operative end first dimension is sized to be received between the adjacent vertebrae in an initial insertion, wherein the slots extend to the distally-located end of the barrel;
   a cannula leading from a proximally-located portion of the barrel to an opening thereof, the opening adjacent the operative end for disposing of the implant material therefrom; and
   an inner member reciprocable within the barrel and having features located on at least one outer surface of the inner member for engaging one or more surfaces of the slots,
   wherein movement of the features against the one or more surfaces expands the distally-located end of the barrel and causes the adjacent vertebrae to become distracted as a result of the expanding surface(s).

2. The surgical device according to claim 1 wherein retraction of the inner member in a direction away from the operative end forces at least the distally-located end of the barrel to become expanded in the first dimension.

3. The surgical device according to claim 1 including one or more stops for maintaining the features of the inner member in a desired position along the length of the elongated barrel.

4. The surgical device according to claim 1 further including a loading chamber for loading of the implant material into the cannula, and wherein the inner member is disposed at least partially in the cannula for advancing the implant material through the barrel.

5. The surgical device according to claim 1 wherein the implant material is advanced through the distally-located end of the barrel to at least partially distract the adjacent vertebrae.

6. A system for distraction and insertion of implant material in an intevertebral space between adjacent vertebrae, the system comprising:
   a surgical device, comprising:
      a barrel comprising a longitudinal length from a distal end to a proximal end; and
      an operative end fixedly attached and integral to the distal end of the barrel, wherein the operative end comprises:
         a longitudinal length from a distal end to a proximal end;
         a first major straight side and a second major straight side each comprising a first dimension;

a first minor straight side and a second minor straight side each comprising a second dimension that is smaller than the first dimension;

a first slot that separates the first major straight side into two parts;

a second slot that separates the second major straight side into two parts;

a third slot that separates the first minor straight side into two parts; and a fourth slot that separates the second minor straight side into two parts, wherein each of the first, second, third, and fourth slots extend to the distal end of operative end; and a cannula, comprising:
  a cannula body that extends along at least a portion of the longitudinal length of the barrel of the surgical device;
  and wherein the cannula comprises at least one expandable mechanism to distract the adjacent vertebrae when an implant material passes therethrough.

7. The system according to claim 6, wherein the surgical device further comprises an inner member reciprocable within the barrel and having features located on at least one outer surface of the inner member for engaging at least one of the first, second, third and fourth slots to expand the operative end of the barrel.

8. The system according to claim 7 wherein the inner member is a rod, and the inner member features comprise one or more contours on the outer surfaces of the rod.

9. The system according to claim 7 wherein movement of the inner member in a direction towards the operative end forces the operative end of the barrel to become expanded.

10. The system according to claim 7 including one or more stops for maintaining the features of the inner member in a desired axial position along the length of the barrel.

11. The system according to claim 7 wherein the surgical device further comprises a loading chamber for loading of the implant material into the cannula, and wherein the inner member is disposed at least partially in the cannula for advancing the implant material through the barrel.

12. The system according to claim 11 wherein the implant material is advanced through the distally-located end of the barrel to at least partially distract the adjacent vertebrae.

* * * * *